(12) United States Patent
Sheridan et al.

(10) Patent No.: US 6,410,316 B1
(45) Date of Patent: Jun. 25, 2002

(54) METHODS FOR PRODUCING A VECTOR PRODUCING CELL LINE UTILIZING A HIGH MULTIPLICITY OF TRANSDUCTION

(75) Inventors: Philip L. Sheridan; Mordechai Bodner, both of San Diego; Nicholas J. DePolo, Solana Beach; Sybille Sauter, Del Mar; Stephen M. W. Chang, Poway, all of CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/526,983

(22) Filed: Mar. 15, 2000

Related U.S. Application Data

(60) Provisional application No. 60/124,468, filed on Mar. 15, 1999.

(51) Int. Cl.[7] .......................... C12N 15/00; C12Q 1/70; C12P 21/04; C07H 21/04; A61K 39/12
(52) U.S. Cl. .................. 435/320.1; 435/5; 435/69.7; 536/23.72; 424/199.1; 424/208.1
(58) Field of Search .................. 435/5, 69.7, 320.1; 536/23.72; 424/199.1, 208.1

(56) References Cited

FOREIGN PATENT DOCUMENTS

| WO | WO 92/05266 | 4/1992 |
|---|---|---|
| WO | WO 97/07225 | 2/1997 |

OTHER PUBLICATIONS

Kotani et al., "Improved Methods of Retroviral Vector Transduction and Production for Gene Therapy" *Human Gene Therapy* 5:19–28, 1994.

Yee et al., "Generation of High–Titer Pseudotyped Retroviral Vectors with Very Broad Host Range" *Methods in Cell Biology* 43:99–112, 1994.

Persons et al., "An Improved Method for Generating Retroviral Producer Clones for Vectors Lacking a Selectable Marker Gene" *Blood Cells, Molecules, and Diseases* 24(9):167–182, May, 1998.

Sheridan et al., "Generation of Retroviral Packaging and Producer Cell Lines for Large–Scale Vector Production and Clinical Application: Improved Safety and High Titer" *Molecular Therapy* 2(3):262–275, Sep., 2000.

*Primary Examiner*—Hankyel T. Park
(74) *Attorney, Agent, or Firm*—Robert P. Blackburn; Louis C. Cullman; Anne S. Dollard

(57) ABSTRACT

Retroviral vector particle producing cells are provided, wherein the cell (a) has greater than 5 stably integrated copies of a retroviral vector construct; (b) produces greater than 10 infectious recombinant retroviral vector particles per cell per day; and (c) produces replication incompetent retroviral vector particles.

15 Claims, 13 Drawing Sheets

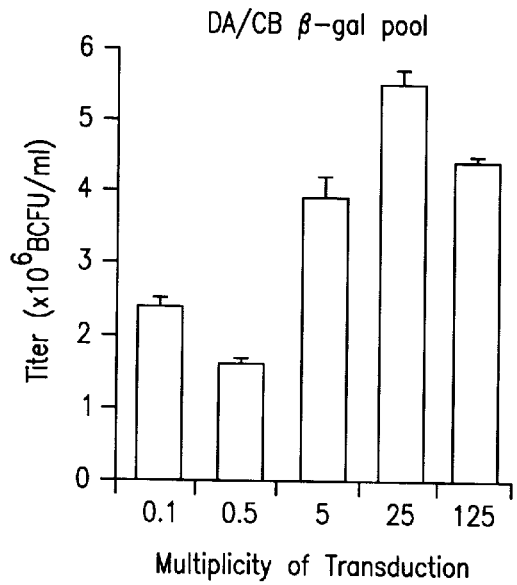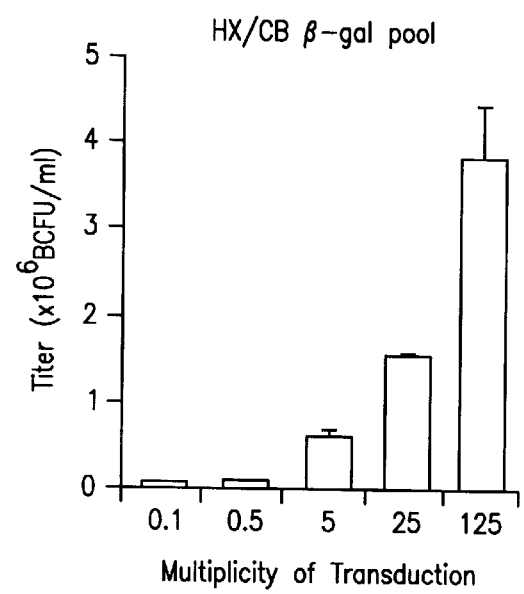
FIG. 3A  FIG. 3B
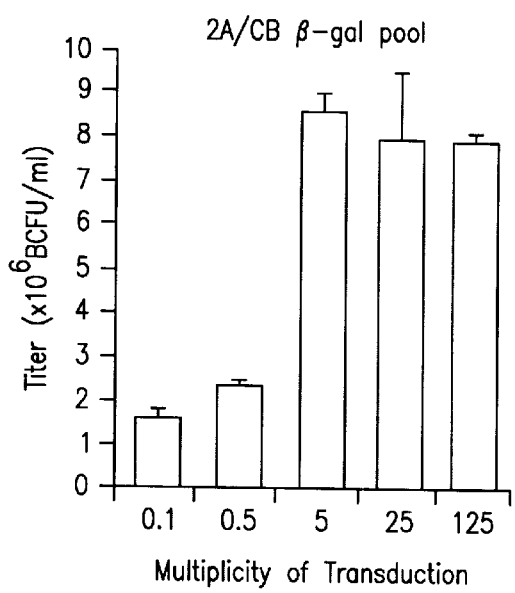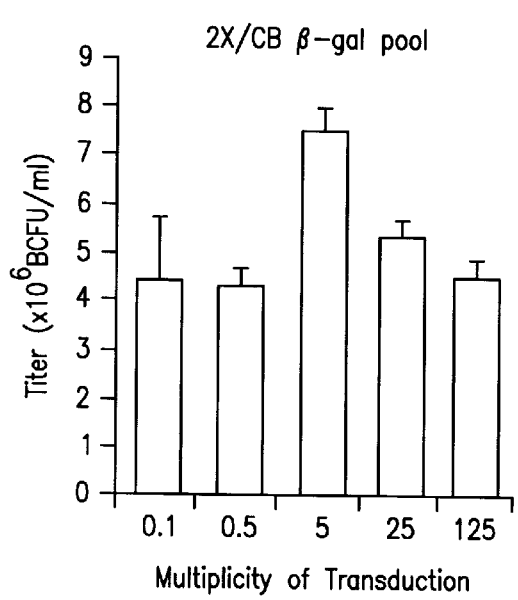
FIG. 3C  FIG. 3D

METHODS FOR PRODUCING A VECTOR PRODUCING CELL LINE UTILIZING A HIGH MULTIPLICITY OF TRANSDUCTION

CROSS-REFERENCE TO RELATED APPLICATION

This application claims priority to U.S. Provisional Patent Application No. 60/124,468, filed Mar. 15, 1999, which application is incorporated herein by reference in its entirety.

TECHNICAL FIELD

The present invention relates generally to compositions and methods with research and pharmaceutical applications, and more specifically, to methods for producing a retroviral vector composition of very high titer.

BACKGROUND OF THE INVENTION

Since the discovery of nucleic acids in the 1940s and continuing through the most recent era of biotechnology, substantial research has been undertaken in order to affect the course of a disease through interaction with the nucleic acids of living organisms. Most recently, a wide variety of methods have been described for altering or affecting genes within humans or animals, by directly administering to the human or animal a nucleic acid molecule which alters or effects the course of a disease. In this regard, many different vectors have been utilized to deliver nucleic acid molecules to a human or animal, including for example, viral vectors derived from retroviruses, adenoviruses, vaccinia viruses, herpes viruses, and adeno-associated viruses (see Jolly, *Cancer Gene Therapy* 1(1):51–64, 1994).

One gene therapy approach which has shown particular promise are recombinantly produced, retroviral vector particles. Briefly, retroviruses are RNA viruses which can replicate and integrate into a host cell's genome through a DNA intermediate. This DNA intermediate, or provirus, may be stably integrated into the host's cellular DNA.

Although retroviruses can cause disease, they also have a number of properties that lead them to be considered as one of the most promising techniques for genetic therapy of disease. These properties include: (1) efficient entry of genetic material (the vector genome) into cells; (2) an active efficient process of entry into the target cell nucleus; (3) relatively high levels of gene expression; (4) minimal pathological effects on target cells; and (5) the potential to target particular cellular subtypes through control of the vector-target cell binding and tissue-specific control of gene expression. In using a retrovirus for genetic therapy, a foreign gene of interest may be incorporated into the retrovirus in place of normal retroviral RNA. When the retrovirus injects its RNA into a cell, the foreign gene is also introduced into the cell, and may then be integrated into the host's cellular DNA as if it were the retrovirus itself. Expression of this foreign gene within the host results in expression of foreign protein by the host cell.

One issue however, that has arisen in developing commercial grade quantities of therapeutic retroviruses, is the ability to make sufficient retroviral vector particles at a suitable concentration to: (1) treat a large number of cells (e.g., $10^8$–$10^{10}$); and (2) manufacture vector particles at a commercially viable cost.

The present invention provides methods for obtaining high titers of retroviral vector particles at a commercially feasible cost, and further provides other related advantages.

SUMMARY OF THE INVENTION

Briefly stated, the present invention provides compositions and methods for producing high titer retroviral vector particles. Within one aspect of the invention retroviral vector particle producing cells are provided, wherein the cell (a) has greater than 5, 6, 7, 8, 9, 10, or, 15 stably integrated copies of a retroviral vector construct; (b) produces greater than 5, 10, 20, 50, 75, 100, 150, or, 200 infectious recombinant retroviral vector particles per cell per day; and (c) produces replication incompetent retroviral vector articles. Preferably, such cells will stably produce infectious recombinant retroviral vector particles over at least 30, 50, 75, or, 100 cell doublings, or alternatively, for greater than 2, 3, 4, or, 5 months in cell culture. Within the context of the present invention, "stable integration of retroviral vector constructs" refers to integration of the retroviral vector construct into the chromosomal DNA of the host cell. Integration of the retroviral vector construct into chromosomal DNA, and determination of copy number may be readily determined by Southern analysis. Production of replication incompetent retroviral vector particles may be readily determined using the *Mus dunni* co-cultivation marker rescue assay provided in example 6. Preferably, vector producing cells of the present invention produce no replication competent retrovirus as determined by the above-noted *Mus dunni* marker rescue assay.

Within various embodiments of the invention, the cell has a stably integrated gag/pol expression cassette, or alternatively, a stably integrated gag expression cassette and a stably integrated pol expression cassette. Further the cell can have a stably integrated env expression cassette.

Also provided by the present invention are methods for producing high titer recombinant retroviral vector particle producing cells, comprising the step of transducing greater than 20, 30, 40, 50, 60, 70, 80, 90, or, 100 recombinant retroviral vector particles per cell into a population of packaging cells. Within another related aspect methods for producing recombinant retroviral vector particle producing cells, comprising transfecting recombinant retroviral vector constructs into a population of packaging cells, wherein at least 5 retroviral vector constructs per cell are stably integrated into said cells. Within certain embodiments, the packaging cell line has a stably integrated gag/pol expression cassette, or alternatively, a stably integrated gag expression cassette and a stably integrated pol expression cassette.

Within yet another aspect of the present invention, methods are provided for producing recombinant retroviral vector particle producing cells, comprising the general steps of (a) generating VSV-G pseudotyped retroviral vector particles; (b) concentrating said particles; and (c) introducing said vector particles into a packaging cell line, such that recombinant retroviral vector particle producing cells are produced.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIGS. 3A, 3B, 3C and 3D are bar graphs which depict the titer and multiplicity of transduction for various packaging cell lines and vectors.

DETAILED DESCRIPTION OF THE INVENTION

Definitions

Figure 1:
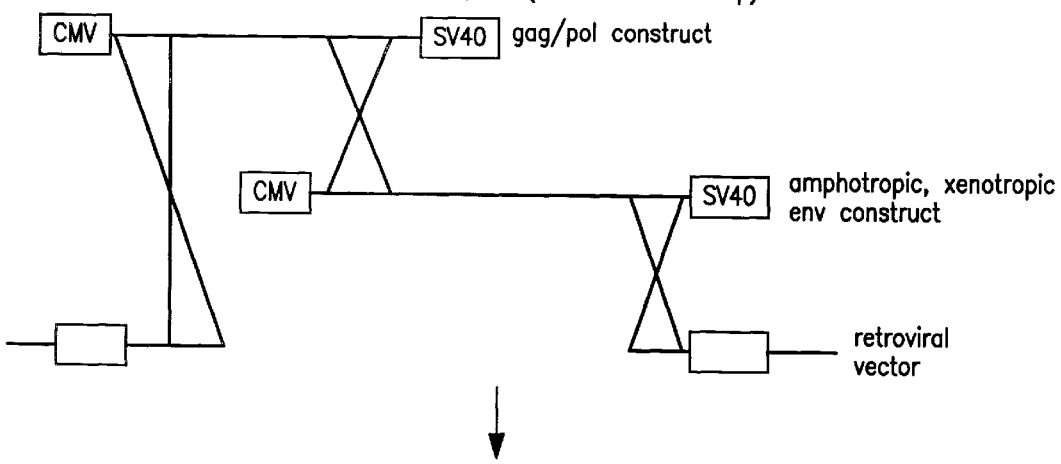
FIG. 1 schematically illustrates the sequence homologies between three retroviral components: env, gag/pol and a retroviral vector construct.
Figure 1:
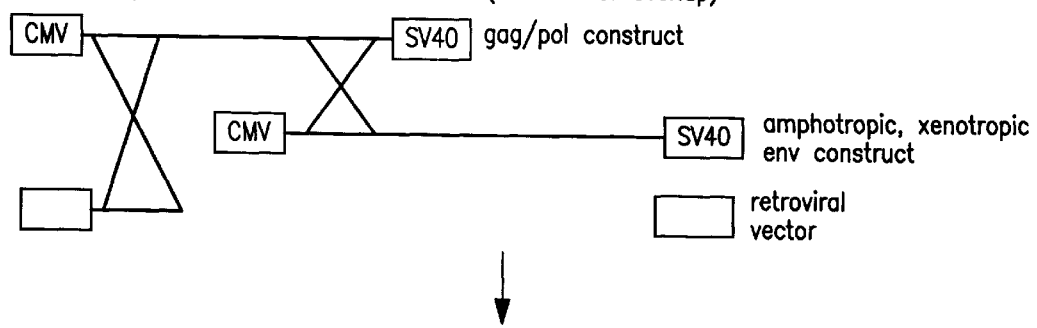
Figure 1:
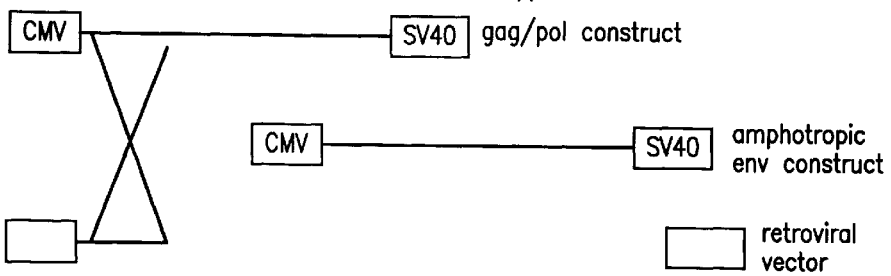

Prior to setting forth the invention, it may be helpful to an understanding thereof to first set forth definitions of certain terms that will be used hereinafter.

"Retroviral vector construct" refers to an assembly which is, within preferred embodiments of the invention, capable of directing the expression of a sequence(s) or gene(s) of interest. Briefly, the retroviral vector construct must include a 5' LTR, a tRNA binding site, a packaging signal, an origin of second strand DNA synthesis and a 3' LTR. A wide variety of heterologous sequences may be included within the vector construct, including for example, sequences which encode a protein (e.g., cytotoxic protein, disease-associated antigen, immune accessory molecule, or replacement gene), or which are useful as a molecule itself (e.g., as a ribozyme or antisense sequence).

The retroviral vector construct may also include transcriptional promoter/enhancer or locus defining element(s), or other elements which control gene expression by means such as alternate splicing, nuclear RNA export, post-translational modification of messenger, or post-transcriptional modification of protein. Optionally, the retroviral vector construct may also include selectable markers such as Neo, TK, hygromycin, phleomycin, histidinol, human placental Alkaline Phosphatase, NGFR or DHFR, as well as one or more specific restriction sites and a translation termination sequence.

"Expression cassette" refers to an assembly which is capable of directing the expression of the sequence(s) or gene(s) of interest. The expression cassette must include a promoter which, when transcribed, is operably linked to the sequence(s) or gene(s) of interest, as well as a polyadenylation sequence. Within preferred embodiments of the invention, both the promoter and the polyadenylation sequence are from a source which is heterologous to the helper elements (i.e., gag/pol and env). Expression cassettes of the present invention may be utilized to express a gag/pol gene or an env gene. In addition, the expression cassettes may also be utilized to express one or more heterologous sequences either from a gag/pol and/or env expression cassette, or from a entirely different expression cassette.

Within preferred embodiments of the invention, the expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

As noted above, the present invention provides compositions and methods for constructing packaging cells which allow the production of high titer recombinant retroviral particles. The following sections describe the preparation of retroviral vector constructs, gag/pol expression cassettes, and env expression cassettes.

1. Construction of Retroviral Vector Constructs

Retroviral vector constructs suitable for use within the present invention may be readily constructed given the disclosure provided here (see also, U.S. Pat. No. 6,013,517). Briefly, retroviral vectors generally comprise a 5' LTR, a tRNA binding site, a packaging signal, an origin of second strand DNA synthesis and a 3' LTR. Preferably, the vector construct lacks gag/pol or env coding sequences.

Retroviral vector constructs may be readily constructed from a wide variety of retroviruses, including for example, B, C, and D type retroviruses as well as spumaviruses and lentiviruses (see RNA Tumor Viruses, Second Edition, Cold Spring Harbor Laboratory, 1985). Briefly, viruses are often classified according to their morphology as seen under electron microscopy. Type "B" retroviruses appear to have an eccentric core, while type "C" retroviruses have a central core. Type "D" retroviruses have a morphology intermediate between type B and type C retroviruses. Representative examples of suitable retroviruses include those described in RNA Tumor Viruses at pages 2–7, as well as a variety of xenotropic retroviruses (e.g., NZB-X1, NZB-X2 and $NZB_{9-1}$ (see O'Neill et al., J. Vir. 53:100–106, 1985)) and polytropic retroviruses (e.g., MCF and MCF-MLV (see Kelly et al., J. Vir. 45(1):291–298, 1983)). Such retroviruses may be readily obtained from depositories or collections such as the American Type Culture Collection ("ATCC"; Rockville, Md.), or isolated from known sources using commonly available techniques.

Particularly preferred retroviruses for the preparation or construction of retroviral vector constructs of the present invention include retroviruses selected from the group consisting of Avian Leukosis Virus, Bovine Leukemia Virus, Murine Leukemia Virus, Mink-Cell Focus-Inducing Virus, Murine Sarcoma Virus, Reticuloendotheliosis virus, Gibbon Ape Leukemia Virus, Mason Pfizer Monkey Virus, and Rous Sarcoma Virus. Particularly preferred Murine Leukemia Viruses include 4070A and 1504A (Hartley and Rowe, J. Virol. 19:19–25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Particularly preferred Rous Sarcoma Viruses include Bratislava, Bryan high titer (e.g., ATCC Nos. VR-334, VR-657, VR-726, VR-659, and VR-728), Bryan standard, Carr-Zilber, Engelbreth-Holm, Harris, Prague (e.g., ATCC Nos. VR-772, and 45033), and Schmidt-Ruppin (e.g. ATCC Nos. VR-724, VR-725, VR-354).

Any of the above retroviruses may be readily utilized in order to assemble or construct retroviral vector constructs, packaging cells, or producer cells of the present invention given the disclosure provided herein, and standard recombinant techniques (e.g., Sambrook et al, *Molecular Cloning. A Laboratory Manual,* 2d ed., Cold Spring Harbor Laboratory Press, 1989; Kunkle, *PNAS* 82:488, 1985). Further, within certain embodiments of the invention, portions of the retroviral vector construct may be derived from different retroviruses. For example, within one embodiment of the invention, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus. Similarly, portions of a packaging cell line may be derived from different viruses (e.g., a gag/pol expression cassette may be constructed from a Moloney Murine Leukemia Virus, and an env expression cassette from a Mason Pfizer Monkey virus).

Within certain embodiments of the invention, retroviral vector constructs are provided which have a packaging signal that extends into gag/pol coding sequence, but does not contain any env coding and/or env non-coding sequence. As utilized within the context of the present invention, a packaging signal should be understood to refer to that sequence of nucleotides which is not required for synthesis, processing or translation of viral RNA or assembly of virions, but which is required in cis for encapsidation of genomic RNA (see Mann et al., *Cell* 33:153–159, 1983; RNA Tumor Viruses, Second Edition, supra). Further, as utilized herein, the phrase "lacks env coding sequences, and/or env non-coding sequences" should be understood to refer to retrovectors which contain less than 20, preferably less than 15, more preferably less than 10, and most preferably less than 8 consecutive nucleotides which are found in a retroviral env gene, and in particular, within env expression cassettes that are used to construct packaging cell lines for the retroviral vector construct. Representative examples of such retroviral vector constructs are set forth in more detail below and in Example 1.

Within further embodiments, retroviral vector constructs are provided comprising a 5' LTR, a tRNA binding site, a packaging signal, an origin of second strand DNA synthesis and a 3' LTR, wherein the retrovector plasmid construct does not contain a retroviral nucleic acid sequence upstream of the 5' LTR. As utilized within the context of the present invention, the phrase "does not contain a retroviral nucleic acid sequence upstream of the 5' LTR" should be understood to mean that the retrovector plasmid construct contains less than 20, preferably less than 15, more preferably less than 10, and most preferably less than 8 consecutive nucleotides which are found in a retrovirus, and more specifically, in a retrovirus which is homologous to the retroviral vector construct, upstream of and/or contiguous with the 5' LTR.

2. Construction of gag/pol Expression Cassettes

As noted above, a variety of gag/pol expression cassettes are provided herein (see also, U.S. Pat. No. 6,013,517) which, in combination with the retroviral vector constructs and env expression cassettes described herein, enable the construction of packaging cell lines and producer cell lines which preclude the formation of replication competent virus. Briefly, retroviral gag/pol genes contain a gag region which encodes a variety of structural proteins that make up the core matrix and nucleocapsid, and a pol region which contains genes which encode (1) a protease for the processing of gag/pol and env proteins, (2) a reverse transcriptase polymerase, (3) an RNase H, and (4) an integrase, which is necessary for integration of the retroviral provector into the host genome. Although retroviral gag/pol genes may be utilized to construct the gag/pol expression cassettes of the present invention, a variety of other non-retroviral (and non-viral) genes may also be utilized to construct the gag/pol expression cassette. For example, a gene which encodes retroviral RNase H may be replaced with genes which encode bacterial (e.g., *E. coli* or *Thermus thermophilus*) RNase H. Similarly, a retroviral integrase gene may be replaced by other genes with similar function (e.g., yeast retrotransposon TY3 integrase).

Within one embodiment, gag/pol expression cassettes are provided comprising a promoter operably linked to a gag/pol gene, and a polyadenylation sequence, wherein the gag/pol gene has been modified to contain codons which are degenerate for gag.

Within other embodiments, overlap between the gag/pol gene and the env gene is eliminated in order to prohibit the possibility of homologous recombination between these two regions. Elimination of such overlap may be accomplished in at least two principal ways: (1) by deleting a portion of the gag/pol gene which encodes the integrase protein, and in particular, that portion of the gene which encodes the integrase protein which overlaps with the env coding sequence, or (2) by selecting codons which are degenerate for integrase and/or env.

Thus, within one embodiment of the present invention gag/pol expression cassettes are provided comprising a promoter operably linked to a gag/pol gene, and a polyadenylation sequence or signal, wherein a 3' terminal end of the gene has been deleted. Within further embodiments, this deletion may not effect the biological activity of the integrase. (The biological activity of integrase may be readily determined by detection of an integration event, either by DNA analysis or by expression of a transduced gene; see Roth et al., *J. Vir.* 65(4):2141–2145, 1991.) As an example, in the Murine Leukemia Virus MoMLV (SEQ ID. NO. 1), the gag/pol gene is encoded by nucleotides 621 through 5834. Within this sequence, the protein integrase is encoded by nucleotides 4610 through nucleotide 5834. A portion of the gag/pol sequence which encodes integrase also encodes env (which begins at nucleotide 5776). Thus, within one embodiment of the invention, the 3' terminal end of the gag/pol gene is deleted or truncated in order to prevent crossover with the env gene.

Within other embodiments of the invention, the gag/pol expression cassette contains a heterologous promoter, and/or heterologous polyadenylation sequence. As utilized herein, "heterologous" promoters or polyadenylation sequences refers to promoters or polyadenylation sequences which are from a different source from which the gag/pol gene (and preferably the env gene and retroviral vector construct) is derived from. Representative examples of suitable promoters include the Cytomegalovirus Immediate Early ("CMV IE") promoter, the Herpes Simplex Virus Thymidine Kinase ("HSVTK") promoter, the Rous Sarcoma Virus ("RSV") promoter, the Adenovirus major-late promoter and the SV 40 promoter. Representative examples of suitable polyadenylation signals include the SV 40 late polyadenylation signal and the SV40 early polyadenylation signal.

3. Construction of env Expression Cassettes

Within other embodiments, env expression cassettes are provided suitable for use, along with retroviral vector constructs and gag/pol expression cassettes, for producing recombinant retroviral vector particles. A wide variety of envelopes may be expressed, including for example envelopes from VSV-G, ecotropic, xenotropic, 10A1 and polytropic MLV envelopes, truncated forms of the HIV env, GALV, BAEV, SIV, FeLV-B, RD114, SSAV, Ebola, Sendai, FPV (Fowl plague virus), and influenza virus. Similarly, genes encoding envelopes from RNA viruses (e.g. RNA virus families of Picornaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Birnaviridae, Retroviridae) as well as from the DNA viruses (families of Hepadnaviridae, Circoviridae, Parvoviridae, Papovaviridae, Adenoviridae, Herpesviridae, Poxviridae, and Iridoviridae) may be utilized. Representative examples include FIV, FeLV, RSV, VEE, HFVW, WDSV, SFV, Rabies, ALV, BIV, BLV, EBV, CAEV, HTLV, SNV, ChTLV, STLV, MPMV, SMRV, RAV, FuSV, MH2, AEV, AMV, CT10, EIAV. In addition to the above hybrid envelopes (e.g. envelope comprising regions of more than one of the above), or cell or tissue specific targeting envelopes may likewise be expressed.

Env expression cassettes may be designed to express no MoMLV noncoding sequences. For example, one method of 5' end modification is to substitute the 5' untranslated RNA leader of MoMLV envelope with an alternate leader. The 5' untranslated RNA sequence can be a leader from another protein or an entirely synthetic leader. The leader may also contain one or more introns. The only requirements for the leader are that it contains a Kozak sequence sufficient for efficient translation of the amphotropic envelope. Representative leader sequences may also include untranslated RNA leaders for envelope proteins from other viruses. Examples of these include Vesicular Stomatitis Virus-G protein (VSV-g), Herpes Simplex Virus (HSV) gB protein, or HSV-gD protein. The 5' untranslated leader sequence is inserted so that it spans the sequence between the eucaryotic promoter start site and the amphotropic envelope start codon.

Heterologous Sequences

As noted above, the retroviral vector constructs, gag/pol expression cassettes, and env expression cassettes of the present invention may contain (and express) one or more heterologous sequences. Briefly, a wide variety of heterologous sequences may be utilized within the context of the present invention, including for example, cytotoxic genes, antisense sequences, sequences which encode gene products that activate a compound with little or no cytotoxicity (i.e., a "prodrug") into a toxic product, sequences which encode immunogenic portions of disease-associated antigens and sequences which encode immune accessory molecules. Representative examples of such genes are described in more detail in U.S. Pat. No. 6,013,517.

Within one embodiment, retroviral vector constructs are provided which direct the expression of one or more heterologous sequences which encode "replacement" genes. As utilized herein, it should be understood that the term "replacement genes" refers to a nucleic acid molecule which encodes a therapeutic protein that is capable of preventing, inhibiting, stabilizing or reversing an inherited or noninherited genetic defect. Representative examples of such genetic defects include disorders in metabolism, immune regulation, hormonal regulation, and enzymatic or membrane associated structural function. Representative examples of diseases caused by such defects include Cystic Fibrosis ("CF"; see Dorin et al., *Nature* 326:614, ), Parkinson's Disease, Adenosine Deaminase deficiency ("ADA"; Hahma et al., *J. Bact.* 173:3663–3672, 1991), b-globin disorders, Hemophilia A & B (Factor VIII-deficiencies; see Wood et al., *Nature* 312:330, 1984), Gaucher disease, diabetes, forms of gouty arthritis and Lesch-Nylan disease (due to "HPRT" deficiencies; see Jolly et al., *PNAS* 80:477–481, 1983) and Familial Hypercholesterolemia (LDL Receptor mutations; see Yamamoto et al., *Cell* 39:27–38, 1984).

Preparation of Retroviral Packaging Cell Lines, and Generation of Recombinant Viral Particles As noted above, the gag/pol expression cassettes and env expression cassettes of the present invention may be used to generate transduction competent retroviral vector particles by introducing them into an appropriate parent cell line in order to create a packaging cell line, followed by introduction of a retroviral vector construct, in order to create a producer cell line (see generally, WO 92/05266).

A wide variety of animal cells may be utilized to prepare the packaging or vector producing cells of the present invention, including for example cells obtained from vertebrates, warm-blooded animals, or, mammals such as human, feline, goat, bovine, sheep, caprine, macaque, dog, rat and mouse cells. Particularly preferred cell lines for use in the preparation of packaging cell lines of the present invention are those that lack genomic sequences which are homologous to the retroviral vector construct, gag/pol expression cassette and env expression cassette to be utilized. Methods for determining homology may be readily accomplished by, for example, hybridization analysis (see Martin et al., *PNAS* 78:4892–4896, 1981; see also WO 92/05266).

Expression cassettes of the present invention may be introduced into cells by numerous techniques, including for example, transfection by various physical methods, such as electroporation, DEAE dextran, lipofection (Felgner et al., *Proc. Natl. Acad. Sci. USA* 84:7413–7417, 1989), direct DNA injection (Acsadi et al., *Nature* 352:815–818, 1991); microprojectile bombardment (Williams et al., *PNAS* 88:2726–2730, 1991), liposomes of several types (see e.g., Wang et al., *PNAS* 84:7851–7855, 1987); CaPO$_4$ (Dubensky et al., *PNAS* 81:7529–7533, 1984), DNA ligand (Wu et al, *J. of Biol. Chem.* 264:16985–16987, 1989), administration of nucleic acids alone (WO 90/11092), or administration of DNA linked to killed adenovirus (Curiel et al., *Hum. Gene Ther.* 3: 147–154, 1992). Expression cassettes may also be introduced into cells via transduction using various viral vectors such as e.g. retroviral, AAV or adenoviral vectors.

Producer cell lines (also called vector-producing lines or "VPCLs") may then be readily prepared by introducing a retroviral vector construct into a packaging cell line via transfection as described above, or, via transduction.

Pharmaceutical Compositions

Within another aspect of the invention, pharmaceutical compositions are provided, comprising a recombinant viral particle as described above, in combination with a pharmaceutically acceptable carrier or diluent. Such pharmaceutical compositions may be prepared either as a liquid solution, or as a solid form (e.g., lyophilized) which is suspended in a solution prior to administration. In addition, the composition may be prepared with suitable carriers or diluents for topical administration, injection, or oral, nasal, vaginal, sub-lingual, inhalant or rectal administration. Methods for the preparation of pharmaceutical preparations are described in more detail within U.S. Pat. No. 6,013,517. Particularly preferred methods and compositions for preserving recombinant viruses are described in U.S. applications entitled "Methods for Preserving Recombinant Viruses" (see WO 94/11414).

Methods

Within other aspects of the present invention, methods are provided for expressing a selected heterologous nucleic acid molecule in a warm-blooded animal, or, to cells in a culture, comprising the step of administering to said animal, or said cells, recombinant retroviral vector particles produced according to the methods provided herein. Representative methods (e.g. methods for inhibiting or destroying a pathogenic agent such as a tumor; for generating an immune response against an immunogenic portion of an antigen; and for delivering replacement genes) are described in more detail in U.S. Pat. No. 6,013,517.

The following examples are offered by way of illustration, and not by way of limitation.

EXAMPLES

The following examples describe the production of high titer retroviral producer cell pools and clones without detectable replication-competent retrovirus (RCR). The method is based on the production and use of high titer retroviral vector with a tropism different from the recipient packaging cell line. This vector preparation is used to transduce retroviral packaging cell lines at a high multiplicity of transduction (mot).

Example 1

Generation of Retroviral Vector Constructs

All retroviral vector constructs were generated using standard molecular biology techniques as described in Sambrook et al., Molecular Cloning: A Laboratory Manual, $2^{nd}$ ed., Cold Spring Harbor Laboratory Press, 1989.

A. Construction of the hGH Expressing Retroviral Vector GH827

The retroviral vector GH827 codes for the human growth hormone gene (hGH) which is transcribed from the 5'LTR, followed by the SV40 promoter driving the neomycin resistance ($neo^r$) gene. The source of the hGH gene is plasmid chGH 800 described in Martial et al., Science 205:602, 1979. Briefly, the cDNA coding for hGH was released from chGH 800 as a Hind III fragment, the ends filled in by Klenow polymerase using standard procedures and the blunted Hind III fragment cloned into Srf I digested K3-L1, resulting in the retroviral vector GH827. Briefly, K3-L1 is derived from the KT-3 retroviral vector coding for HIVgag/protease which is transcribed from the 5' LTR and followed by the SV40 promoter which drives the $neo^r$ gene (KT-3 is described in U.S. application Ser. No. 07/965,084, filed Oct. 22, 1992, which is a continuation of U.S. application Ser. No. 07/586,603 (now abandoned), which is a continuation-in-part of U.S. application Ser. No. 07/565,606, filed Aug. 10, 1990 (now abandoned), which is a continuation-in-part of U.S. application Ser. No. 07/395,932, filed Aug. 18, 1989, which is a continuation-in-part of U.S. application Ser. No. 07/170,515, filed Mar. 21, 1988 (now abandoned). An L1 linker introducing the restriction enzyme sites 5'-Xho I-Bam HI-Srf I-Not I-Cla I-Sal I 3' was engineered such that it can be cloned into a Cla I site at the 3' end. The L1 linker was cloned into the Xho I and Cla I digested KT-3 which released the HIVgag/protease gene and replaced it with the L1 linker, resulting in K3-L1.

B. Construction of the b-gal Expressing Retroviral Vector pCBb-gal

The retroviral vector pCBb-gal codes for the b-galactosidase gene which is transcribed from the 5'LTR and followed by the SV40 promoter driving the $neo^r$ gene. The construction of the retroviral vector pCBb-gal is described in Irwin et al., J. Virol. 68:5036–5044, 1994.

C. Construction of the Human Factor VIII Expressing Retroviral Vector pCF8

The retroviral vector pCF8 codes for a truncated form of the human factor VIII gene which is transcribed from the 5'LTR. The source for the human factor VIII gene is Chiron's proprietary plasmid pSV7dF8-300. The identical coding region of the truncated human factor VIII gene as described before (U.S. Ser. No.08/696,381, filed Aug. 13, 1996 which is a continuation-in-part→CIP→CIP to U.S. Ser. No. 08/367,071, filed in Dec. 30, 1994) was cloned into a "cross-less" retroviral vector derived from pBA-5b (described in U.S. Pat. No. 6,013,517), resulting in the retroviral vector pCF8.

D. Construction of the Rat IL-4 Expressing Retroviral Vector pBA-9b/rIL-4

The retroviral vector pBA-9b/rIL-4 codes for the rat interleukin-4 (rIL-4) gene which is transcribed from the 5'LTR. To isolate the rat IL-4 cDNA, rat splenocytes were removed and stimulated in culture for 48 hours with recombinant rat IL-4 (R&D Systems Inc., Minneapolis, Minn.). Cells were harvested and mRNA isolated using the RNA/DNA Midi Kit (Qiagen Inc., Valencia, Calif.). IL-4-specific oligonucleotide primers were produced by Operon Technologies Inc. (Alameda, Calif.) by using sequences published by McKnight et al., Eur. J. Immunol. 21:1 187, 1991. The forward primer introduces a Xho I restriction enzyme site (SEQ ID NO. 1; ATA <u>CTC GAG</u> TCT CAC GTC ACT GAC TG; Xho I site underlined) and the reverse primer introduces a Hind III recognition site (SEQ ID NO. 2; CGC <u>AAG CTT</u> CTA TTA GGA CAT GGA AG; Hind III site underlined).

The reverse primer was used, with the rat spleen mRNA as template, in a reverse transcription reaction using standard procedures to generate rIL-4 cDNA. This material was then amplified by polymerase chain reaction (PCR), using both oligonucleotides. This rIL-4 cDNA insert was cloned into the Xho I and Hind III digested retroviral vector pBA-9b, resulting in pBA-9b/rIL-4. pBA-9b is based on pBA-5b (see U.S. Pat. No. 6,013,517 entitled "Crossless Retroviral Vectors") with additional restriction enzyme sites in the multiple cloning site. Fidelity of the rIL-4 cDNA insert was confirmed by DNA sequencing (SeqWright, LLC, Houston, Tex.).

E. Construction of the eGFP Expressing Retroviral Vector pBA-9b/eGFP

The retroviral vector pBA-9b/eGFP codes for the enhanced green fluorescent protein (eGFP) which is transcribed from the 5'LTR. The eGFP cDNA was derived from Clontech's GFP S65T plasmid (Clontech Laboratories Inc., Palo Alto, Calif.). Briefly, the 747 nt Hind III and Xba I fragment of the GFP S65T coding for the eGFP cDNA was ligated into the Hind III and Xba I digested adenoviral vector pAdRSVmcspA#4 to create pAdRSVhGFPpA (a kind gift of Drs B. Davidson and R. D. Anderson, University of Iowa). Plasmid pAdRSVhGFPpA was digested with Xho I and Not I to release the eGFP cDNA and the fragment cloned into Xho I and Not I digested retroviral vector pBA-9b (Example 1D), resulting in pBA-9b/eGFP.

Example 2

Generation of Retroviral Packaging Cell Lines

All retroviral packaging cell lines (PCL) described in this example were constructed using the "split genome" approach with the retroviral gag/pol and env genes each contained on a separate expression cassette. The gag/pol gene is derived from the Moloney Murine Leukemia Virus (MoMLV) and the env gene is derived from either the amphotropic MLV 4070A or the xenotropic MLV strain NZB9-1. A number of gag/pol and env cassettes with differing lengths of the 5' and 3' untranslated regions (UTR) as well as one gag/pol construct truncated in the 3' coding region were introduced into canine and human parent cell lines.

Introduction of the third viral component into a PCL, the retroviral vector cassette, results in a vector producing cell (VPCL). Various combinations of gag/pol, env and the retroviral vector component result in different degrees of sequence overlap between the three viral components. A safety benefit of this configuration is that three recombination events between these retroviral components are required to generate a replication competent retrovirus (RCR). In some PCLs, however, one or more of these three areas of sequence overlap are eliminated or reduced, thereby preventing RCR formation even in the case of homologous recombination in the remaining areas of overlap. FIG. 1 illustrates the extent of overlap between the three viral components in the various VPCL systems.

A. Production of Packaging Cell Line DA

The packaging cell line DA was produced by the sequential incorporation of the amphotropic envelope cassette derived from 4070A (Chattopadhyay et al., *J. Virol* 39:777, 1981) and the gag/pol cassette derived from MoMLV (Miller et al., *Mol. Cell. Biol.* 5:431, 1985) into the canine sarcoma parent cell line D-17 (ATCC CCL 183). Both expression cassettes as well as the production of the DA PCL are described in PCT publication no. WO 92/05266. Retroviral producer lines based on DA have three areas of sequence homology between the three retroviral components.

B. Production of Packaging Cell Line 2A

The packaging cell line 2A was produced by the sequential incorporation of the amphotropic envelope cassette derived from 4070A (Chattopadhyay et al., *J. Virol.* 39:777, 1981) and the gag/pol cassette derived from MoMLV (Miller et al., *Mol. Cell. Biol.* 5:431, 1985) into the human kidney parent cell line 293 (ATCC CRL 1573). Both expression cassettes as well as the production of the 2A PCL are described in PCT# WO 92/05266. Retroviral producer lines based on 2A have three areas of sequence homology between the three retroviral components.

C. Production of Packaging Cell Line HA

The packaging cell line HA was produced by the sequential incorporation of the amphotropic envelope cassette derived from 4070A (Chattopadhyay et al., *J. Virol.* 39:777, 1981) and the gag/pol cassette derived from MoMLV (Miller et al., *Mol. Cell. Biol.* 5:431, 1985) into the human fibrosarcoma parent cell line HT-1080 (ATCC CCL 121). Both expression cassettes are described in PCT# WO 92/05266, except, that the envelope cassette in HA was shortened by 441 nt in the 5' untranslated region at the Eag I sites in comparison to pCMV envam Dra described in PCT# WO 92/05266. The production of the HA PCL followed the description for PCL production outlined in PCT# WO 92/05266. Retroviral producer lines based on HA have three areas of sequence homology between the three retroviral components.

D. Production of Packaging Cell Line HX

The packaging cell line HX was produced by the sequential incorporation of the xenotropic envelope cassette derived from NZB9-1 (O'Neill et al., *J. Virol.* 53:100, 1985) and the gag/pol cassette derived from MoMLV (Miller et al., *Mol. Cell. Biol.* 5:431, 1985) into the human fibrosarcoma parent cell line HT-1080 (ATCC CCL 121). Both expression cassettes as well as the production of the HX PCL are described in PCT# WO 92/05266. Retroviral producer lines based on HX have three areas of sequence homology between the three retroviral components.

E. Production of Packaging Cell Line 2X

The packaging cell line 2X was produced by the sequential incorporation of the xenotropic envelope cassette derived from NZB9-1 (O'Neill et al., *J. Virol.* 53:100, 1985) and the gag/pol cassette derived from MoMLV (Miller et al., *Mol. Cell. Biol.* 5:431, 1985) into the human kidney parent cell line 293 (ATCC CRL 1573). Both expression cassettes are described in PCT# WO 92/05266. The production of the 2X PCL followed the description for PCL production outlined in PCT# WO 92/05266. Retroviral producer lines based on 2X have three areas of sequence homology between the three retroviral components.

F. Production of Packaging Cell Line 2A-LB

The packaging cell line 2A-LB was produced by the sequential incorporation of the amphotropic envelope cassette derived from 4070A (Chattopadhyay et al., *J. Virol.* 39:777, 1981) and the gag/pol cassette derived from MoMLV (Miller et al., *Mol. Cell. Biol.* 5:431, 1985) into the human kidney parent cell line 293 (ATCC CRL 1573). The gag/pol cassette pSCV10 is described in PCT# WO 92/05266 and the amphotropic envelope cassette pCMVen-v$^{am}$ Dra/LBGH is described in U.S. Pat. No. 6,013,517. The production of the 2A-LB PCL followed the description for PCL production outlined in PCT# WO 92/05266. Retroviral producer lines based on 2A-LB have two areas of sequence homology between the three retroviral components.

G. Production of Packaging Cell Line HA-LB

The packaging cell line HA-LB was produced by the sequential incorporation of the amphotropic envelope cassette derived from 4070A (Chattopadhyay et al., *J. Virol.* 39:777, 1981) and the gag/pol cassette derived from MoMLV (Miller et al., *Mol. Cell. Biol.* 5:431, 1985) into the human fibrosarcoma parent cell line HT-1080 (ATCC CCL 121). The gag/pol cassette pSCV10 is described in PCT# WO 92/05266 and the amphotropic envelope pCMVenv$^{am}$Dra/LBGH is described in U.S. Pat. No. 6,013,517. The production of the HA-LB PCL followed the description for PCL production outlined in PCT# WO 92/05266 and U.S. Pat. No. 6,013,517. Retroviral producer lines based on HA-LB have two areas of sequence homology between the three retroviral components.

H. Production of Packaging Cell Line HAII

The packaging cell line HAII was produced by the sequential incorporation of the amphotropic envelope cassette derived from 4070A (Chattopadhyay et al., *J. Virol.* 39:777, 1981) and the gag/pol cassette derived from MoMLV (Miller et al., *Mol. Cell. Biol.* 5:431, 1985) into the human fibrosarcoma parent cell line HT-1080 (ATCC CCL 121). The gag/pol cassette pSCV10/5',3'tr. and the amphotropic envelope cassette pCMVb/env$^{am}$ are described in U.S. Pat. No. 6,013,517. The production of the HAII PCL is described in detail in U.S. Pat. No. 6,013,517. Retroviral producer lines based on HAII have only one area of sequence homology between the three retroviral components.

Example 3

Determination of Retroviral Vector Titer

The titer of retroviral vectors was determined by either transfer of expression analysis (TOE titer), PCR quantitation (PCR titer, automated PCR titer) using one, both or all three titering methods. All three titer assays start by transducing target cells with the retroviral sample, which for example is the filtered (0.45 um) media supernatant, harvested from vector producing pools or clones. In the TOE titer assay, the presence of the integrated provector is detected indirectly by measuring the expression of the gene of interest. In the PCR titer assays, the presence of the integrated provector in form of DNA is itself directly detected.

A. (TOE) Transfer of Expression Titer Assay

This general titering assay utilizes HT-1080 target cells seeded at $5\times10^4$ or $3\times10^5$ cells/well in either a 24- or 6-well plate format, respectively. The cells are seeded one day prior to transduction in 0.5 or two ml of media, respectively. Then the target cells are transduced with retroviral supernatant in the presence of 8 ug/ml polybrene. Transduction is allowed to occur for 24 hours at 37° C. after which fresh media is added. Target cell supernatants are then assayed at specific times post-transduction for relative transgene expression as specified by the biochemical or functional assay described below. The TOE titer value is given in colony forming units/ml or cfu/ml.

A-1. Human Growth Hormone (hGH) TOE Titer Assay

The hGH TOE titer assay was carried out using the TGES kit (Nichol's Institute Diagnostics, San Juan Capistrano, Calif.) in order to quantify hGH levels in culture cell media. The HT-1080 target cells are transduced with retroviral vectors coding hGH and their supernatant is tested 24 hours post-transduction. The kit supplies inert beads coated with anti-hGH antibody for capture and a secondary antibody isotopically labelled with $S^{32}$ for detection. The beads are incubated in a mixture containing the supernatant sample and the secondary antibody for one hour, washed and counted in a gamma-counter as instructed by the manufacturer. hGH standards are supplied in the kit and hGH sample levels are calculated from the standard curve.

A-2. b-Galactosidase TOE Titer Assay

There are two ways to determine the retroviral b-gal TOE titer. The first titer assay is a biochemical staining procedure called x-gal stain resulting in blue cells whenever b-galactosidase is expressed intracellularly. The second titer assay is based on a chemiluminescent detection method (Galacto-Light) and will be referred to as Galacto-Light titer named after the manufacturer's kit.

In the x-gal stain procedure, the transduced target cells are stained 48 hours post-transduction as follows. The media is removed and 1 ml of the fixing solution added (fixing solution: 2% (v/v) formaldehyde, 0.2% (v/v) glutaraldehyde in PBS), incubated for 5 minutes, drained, fixed cells washed with PBS and 1 ml staining solution added and incubated at 37° C. until color development is completed (staining solution: 5 mM potassium ferrocyanide, 5 mM potassium ferrocyanide, 2 mM MgCl2 and 1 mg/ml x-gal). Because single transduction cells divide in the 48-hour period before staining, blue cell colonies are counted and the retroviral titer determined and expressed in colony-forming units/ml supernatant which equals the titer.

In the Galacto-Light procedure which has been described previously by McCormack et al., *Human Gene Therapy* 8:1263, 1997, the transduced target cells are treated as described in the manufacturer's instructions (Galacto-light Plus kit by Tropix Inc., Bedford, Mass.). Briefly, transduced target cells are washed with PBS, lysed, cell debris removed by spinning the lysate, lysate added to the substrate in the reaction buffer and the luminescence read in the ML3000 luminometer. The luminescence generated by dilutions of vector supernatant is compared to a standard curve generated by dilutions of a processed b-galactosidase vector of known titer, determined by the x-gal staining procedure described above.

A-3. Human Factor VIII TOE Titer Assay

The human factor VIII (hFVIII) TOE titer assay was determined using a commercial diagnostic kit by Chromogenix (Sweden) which directly measures hFVIII functional activity. This is a diagnostic kit which detects the level of hFVIII in plasma or supernatant samples where hFVIII acts as a nonenzymatic cofactor, together with Ca++ and phospholipids, for activated factor IX (FIXa) conversion of factor X to activated FX (FXa). FXa then cleaves a chromogenic substrate which can be spectrophotometrically detected.

For evaluating hFVIII activity, duplicate wells of target cells are transduced with three different volumes of sample viral supernatant at an estimated multiplicity of transduction of 0.01–3. Following 24 hours of transduction, fresh media is applied, and 25 ul of the target cell supernatants assayed in the in vitro kit 48–72 hours post-transduction.

Importantly, the viral supernatant samples are directly compared in this assay to the known processed hFVIII standard DA/B-del-1 (described in WO 98/00541) which generates a linear hFVIII expression standard curve between $3\times10^3–1\times10^6$ cfu/ml. In order to fall within the standard curve, vector samples are generally diluted such that the mot for the target cell transduction is between 0.01–3. The standard DA/B-del-1 hFVIII VPCL clone was produced from an amphotropic dog PCL and has a TOE titer of $1\times10^7$ cfu equivalents/ml. The DA/B-del-1 hFVIII vector does not have a marker gene, and its titer is expressed as equivalency units as follows: 1 equivalency unit is the actual DA/B-del-1 hFVIII expression unit/PCR titer unit which has been determined and standardized to the PCR titer unit/neomycin unit of the CBb-gal vector which contains the $neo^r$. The $neo^r$ titer for CBb-gal is determined by G418 selection in a colony forming assay, and has been determined to be equal to its PCR titer. Therefore, CBb-gal PCR titer/neo titer=1 and allows for the correlation of the DA/B-del-1 TOE hFVIII titer to PCR titer.

A-4. Rat IL-4 TOE Titer Assay

The rat IL-4 TOE titer was determined using an ELISA (Enzyme Linked Immunosorbent Assay) that was developed for this TOE titer assay. Briefly, serial dilutions of vector samples are prepared and a fixed volume added to target cells. Appropriate dilutions of a vector standard, whose titer has been previously determined using the PCR titer assay described below, are also added to the cells and 24 hours later fresh media supplied. After 48 hours, aliquots of supernatant are harvested and rat IL-4 levels determined using the ELISA described below.

Rat IL-4 in cell culture supernatants is detected using a capture ELISA developed for this purpose. Wells of a 96-well polystyrene plate (Costar #3591) are coated overnight at 4° C. with 100 ul of affinity-purified goat anti-rat IL-4 IgG (R&D Systems #AF-504-NA), at 2 ug/ml in PBS containing 0.1% NaAzide. 100 ul block solution (2% teleost skin gelatin, Sigma, in PBS/azide) is added, incubated for 1 hour and plates washed wit PBS containing 0.05% Tween-20. Aliquots of cell culture supernatants are transferred to the coated wells. If necessary, samples may be diluted in an ELISA dilution buffer comprised of PBS with 0.05% Tween-20; 2.5% FCS, 0.5% (w/v) human serum albumin; 1% (w/v) teleost gelatin. After incubating for 5 hours at 37° C. , plates are washed and 100 ul of purified monoclonal mouse anti-rat 11–4 antibody (PharMingen, San Diego, Calif. diluted 1:1, 000 in ELISA dilution buffer, is added. After 1 hour at 37°

C., plates are washed and 100 ul horseradish-peroxidase (HRP) conjugated goat anti-mouse IgG1 (Southern Biotechnologies), 1:1,000 in ELISA dilution buffer, is added. After 1 hour at 37° C. , plates are washed, and TMB substrate (BioRad) is added and after 7 minutes, an equal volume of 1 N H2SO4 is added. Optical density is read at 450 nm.

A-5. Neomycin TOE Titer (neo$^r$) Assay

The neo$^r$ TOE titer procedure is based on the toxicity of the antibiotic G418 to mammalian cells that do not express the neomycin resistance gene. HT-1080 target cell are seeded at $2\times10^5$ cells/well of a 6-well plate. 24 h later, cells are transduced with the retroviral vector coding for neomycin. 24 h post-transduction, the selection marker G418 is added to the media at 0.8 mg/ml and transduced cells will grow into visible colonies whereas untransduced cells will die over the next 10 days. G418-resistant colonies are stained with Coomassie blue, the colonies counted and the neo$^r$ titer determined.

A-6. eGFP TOE Titer Assay

The eGFP TOE titer procedure is based on the detection of the eGFP protein in transduced HT-1080 cells using the FACS (Fluorescence Activated Cell Sorter). HT-1080 cells are seeded at $3\times10^5$ cells/well of a 6-well plate. 24 hours later, the target cells are transduced with dilutions of the retroviral vector preparation and 48 hours post-transduction, the transduced cells are analyzed in the FACS. The titer is determined by back-calculating from the number of % transduced cells considering number of target cells and used volume of the retroviral vector preparation at the time of transduction.

B. Determination of Titer by PCR (Polymerase Chain Reaction)

A more accurate way of determining viral transduction potential is by measuring the actual number of provector copies by Southern or PCR quantitation. This way one can express the viral titer in terms which are more reflective of the actual number of integration events per ml of retroviral preparation. This assay also utilizes the same target cells transduced in the TOE titer assay. However, in this assay the transduced target cell samples are compared directly to target cells transduced with the CBb-gal standard clone and PCR titer units directly correlated to neomycin colony forming units.

Briefly, HT-1080 target cells are transduced as described above, the transduced target cells harvested, their genomic DNA isolated and quantitated against calf thymus DNA standards using the CytoFluor II (PerSeptive Biosystems, Framingham, Mass.) for DNA quantitation after staining the DNA with Hoechst dye H33258 as recommended by manufacturer (Hoechst). Each DNA sample is normalized to 5–7 ng/ml and then triplicate aliquots PCR amplified in the presence of (32P)a-dCTP using primers specific to the MoMLV 5'LTR and packaging region. The amplification reactions are blotted onto DE81 membrane, washed with NaPO$_4$/NaCl buffer and quantitated by phosphorimaging analysis (Molecular Dynamics, Sunnyvale, Calif.). This assay has a liner range of $1\times10^4$–$1\times10^6$ cfu/ml.

C. Determination of Titer by Automated PCR (Polymerase Chain Reaction)

In contrast to the PCR titer described in Example 3B, an automated PCR titer determination has several advantages such as increased sensitivity and accuracy as well as extremely high reproducibility while replacing a relatively subjective read-out by accurate analysis using the PE ABI Prism 7700 system (Perkin-Elmer Corp., Norwalk, Conn.). This automated PCR titer analysis is referred to as PCR titer (auto) and results described in Table 9. Briefly, provector copy numbers are determined in genomic DNA prepared from tissue culture cells after transduction with test sample and standard vector dilutions. Employing a PE ABI Prism 7700 system, equal amounts of genomic DNA are amplified by PCR using a synthetic oligonucleotide primer set directed against the retroviral packaging signal sequences. A synthetic oligonucleotide probe with a 5' fluorescent reporter dye and a 3' quencher dye that hybridizes specifically to sequences between the primer set is also used. During PCR amplification, the endogenous nuclease activity of Taq polymerase cleaves only annealed probe molecules thereby separating reporter and quencher dye.

Example 4

Production of VSV-G Pseudotyped Retroviral Supernatant

The scope of the work described in Examples 4 and 5 includes modifications to the general guidelines reported by Yee et al. *Meth. Cell Biol.* 43: 99, 1994.

In brief, "pseudotype formation", the production of progeny virions containing the genome of one virus encapsidated by the envelope proteins of another (in this case Vesicular Stomatitis Virus glycoprotein, VSV-G), allows for the production of retroviral vectors with an altered and very wide host range. Due to the toxicity of VSV-G, VSV-G pseudotyped vector production is carried out by transient co-transfection of the VSV-G plasmid together with a specific retroviral vector into 293-based human gag/pol intermediates or PCLs which stably express the viral envelope, structural and enzymatic proteins.

For large scale production of transient VSV-G pseudotyped retroviral supernatant, 293-based cell lines such as 293(2–3) (Burns et al., *PNAS* 90:8033, 1993) or 2A-LB (Example 2F) cells were plated into five T225 flasks at $1\times10^7$ cells/flask. 12–24 hours later the cells are transfected for 6–12 hours with the respective retroviral vector and a VSV-G coding plasmid such as pMLG-G (Emi et al., *J. Virology* 65, 1202, 1991) or pCMV-G (see U.S. Pat. No. #5,670,354) using a CaPO4 transfection procedure. The CaPO4 transfection can be carried out using standard procedures or using Promega's Profection kit following manufacturer's instructions (Promega Corp., Madison, Wis.). Following the incubation with the DNA precipitate, the DNA suspension is removed and 30 ml of fresh media per flask applied. 6–20 hours later, the supernatant is collected and 30 ml of fresh media applied for subsequent supernatant collections for 2–3 days or until most of the transfected cells have lifted off the plastic support.

Example 5

Concentration of VSV-G Pseudotyped Retroviral Supernatant

Retroviral vectors can be purified and concentrated by a number of means, including PEG precipitation, centrifugation, ultrafiltration, ion exchange chromatography, size exclusion chromatography, affinity chromatography and sucrose gradient (Aboud et al., *Arch. Virology* 71:185, 1982; U.S. Pat. No. 5,661,022; Bowles et al., *Human Gene Therapy* 7:1735, 1996; U.S. Pat. No. 5,447,859). In addition, viral particles can potentially be concentrated during a lyophylization process (U.S. Pat. No. 5,792,643). In this example, we are describing procedures for the purification and concentration of VSV-G pseudotyped vectors which can also be applied for retroviral vectors with another tropism. These VSV-G pseudotyped viral supernatants can be concentrated as much as 2000-fold without significant loss of titer.

A. Concentration of VSV-G Pseudotyped Supernatant by Centrifugation

Typically, 400–600 ml of harvested, pooled and filtered (0.45 um) VSV-G-supernatants are spun in a GS3 rotor (Sorvall RC 5B Plus centrifuge) and concentrated by overnight centrifugation at 9,000×g for 8–18 hours (Burns et al., *PNAS* 90:8033, 1993). The spent media is decanted off and the "invisible" pellets resuspended in 10–30 ml fresh media or PBS/lactose buffer, aliquoted and then frozen under liquid nitrogen and stored in small aliquots at −80° C. This concentrated viral supernatant is then evaluated for titer by TOE and/or PCR titer analysis before using the vector preparation in the high moi generation of VPCL producer pools and clones. An example for the concentration of VSV-G pseudotyped pCF8 retroviral vector (Example 1C) is given in Table 1.

TABLE 1

Processing steps, recovery and titer of VSV-G/hFVIII retroviral supernatant concentrated by centrifugation

| VSV-G/hFVIII vector material | Amount (ml) | TOE Titer (cfu/ml) | Concentration of titer (x-fold) | % Overall recovery |
|---|---|---|---|---|
| Crude supernatant | 420 | $3.0 \times 10^6$ | | |
| Final product | 30 | $2.5 \times 10^7$ | 8 | 59 |

B. Concentration of VSV-G Pseudotyped Supernatant by PEG

In this example, VSV-G pseudotyped vector particles are concentrated by PEG precipitation alone. The VSV-G pseudotyped vector preparation is clarified by a 0.45 um filtration step. The clarified sample is treated with 10% PEG (polyethylene glycol in PBS) overnight before the precipitates that contain the vector particles are collected by centrifugation (6,000 rpm for 10 minutes in a GS-3 rotor, Sorvall). The PEG pellet is resuspended in PBS/lactose buffer and stored at −80° C. in small aliquots.

C. Concentration of VSV-G Pseudotyped Supernatant by PEG/Centrifugation

In this example, VSV-G pseudotyped vector particles are concentrated by PEG concentration followed by a centrifugation step. The VSV-G pseudotyped vector preparation is concentrated by PEG precipitation as described in Example 5B and then subjected to another round of centrifugation to pellet the vector particles. This final centrifugation is carried out at 6,000 rpm for 18–24 hours or at 14,000 rpm for 1 hour using the GS-3 rotor (Sorvall). The pellet is resuspended in PBS/lactose buffer and stored at −80° C. in small aliquots.

D. Concentration of VSV-G Pseudotyped Supernatant by PEG/Ion Exchange

This example describes the concentration of VSV-G pseudotyped viral vector particles by PEG precipitation followed by purification on an ion exchange column. Transiently produced VSV-G pseudotyped vector was harvested, filtered (0.45 urn Nalgene filter) and precipitated for at least 6 h at 4° C. in the presence of 10% PEG final concentration. The PEG-precipitate containing the viral particle is pelleted by centrifugation for 15 minutes at 3,000 rpm in a Sorvall tabletop centrifuge. The pellet is resuspended in PBS and the equivalent of 50 ml crude supernatant applied to a DEAE column (Toyopearl DEAE-650C, Tosohaas, Montgomeryville, Pa.) with 4 ml bed volume. The column is then washed with PBS and the virus eluted with PBS/500 mM NaCl. The vector particles are spun down in an Eppendorf centrifuge for 1 hour at 4° C. and 14,000 rpm. The pellet is resuspended in PBS/lactose and stored at −80° C. in small aliquots.

E. Concentration of VSV-G Pseudotyped Supernatant by Ultrafiltration Centrifugation This example describes the concentration of VSV-G pseudotyped viral vector particles by an ultrafiltration process. A centrifugation process may follow the ultrafiltration. The process of ultrafiltration is described in the patent "Production and Administration of High Titer Recombinant Retroviruses"Ser. No. 08/367,071. Briefly, the retroviral supernatant is first clarified through a 0.8 um filter connected in series with a 0.65 um filter (Sartorious). This filter arrangement provides approximately 0.5 square feet of filter, and allows processing of about 10 liters of material before clogging. Preferably, after clarification, the filter is rinsed with buffer (PBS). Following clarification, recombinant retroviruses are concentrated by tangential flow ultrafiltration utilizing the hollow fiber tangential flow units (AG Technologies) with a 500,000 molecular weight cut off. Utilizing a pressure differential of 2 psi between filtrate (8 psi) and retentate (10 psi), up to 80 liters of material may be concentrated to a volume of less than 500 ml in under two hours. The material that underwent ultrafiltration can be further concentrated by a centrifugation step as described in Example 5A.

Table 2 below summarizes the results of the purification and concentration procedure of VSV-G pseudotyped pBA-9b/eGFP vector by above described ultrafiltration and centrifugation. A TOE titer analysis (Example 3A-6) was carried out at various steps to determine % recoveries.

TABLE 2

Processing steps, recoveries and titer of VSV-G/eGFP retroviral supernatant concentrated by ultrafiltration and centrifugation

| VSV-G/eGFP vector material | Amount (ml) | TOE Titer (cfu/ml) | Concentration of titer (x-fold) | % step recovery | % Overall recovery |
|---|---|---|---|---|---|
| Crude supernatant | 6,000 | $8.3 \times 10^5$ | | | |
| Clarified supernatant | 6,000 | $5.8 \times 10^5$ | | 70 | |
| Ultrafiltrate | 600 | $4.3 \times 10^6$ | 10 | 74 | |
| Final product | 3 | $5.2 \times 10^8$ | 200 | 60 | 31 |

Example 6

Testing of VPCL Pools and Clones for Replication Competent Retrovirus

This example describes the testing of retroviral VPCL pools for replication competent retrovirus (RCR) with a very sensitive assay called the RCR co-cult marker rescue assay. Briefly, a set number of cells, depending on the scale of the assay, e.g. $1 \times 10^7$ vector-producing cells are co-cultivated with an equal number of *Mus dunni* cells (Lander and Chattopadhyay, *J. Virol.* 52:695, 1984). *Mus dunni* cells are particularly preferred for helper virus detection because they are sensitive to nearly all murine leukemia-related viruses, and contain no known endogenous viruses. At three, six, and nine days after the initial culture, the cells are split approximately 1 to 10. Fifteen days after the initial co-cultivation of *Mus dunni* cells with the vector-producing cells, supernatant fluid is removed from cultures, filtered through a 0.45 mm filter, and subjected to a marker rescue assay.

The MdH Marker Rescue assay has been described previously by Printz et al., *Gene Ther.* 2:143, 1995. Briefly, culture fluid is removed from a MdH tester cell line (*Mus dunni* cells containing pLHL, a hygromycin resistance marker retroviral vector; see Palmer et al., *PNAS* 84(4) :1055–1059, 1987) and replaced with the culture fluid to be tested. Polybrene is added to a final concentration of 4 ug/ml. On day 2, medium is removed and replaced with 2 ml of fresh DMEM containing 10% Fetal Calf Serum. On day 3, supernatant fluid is removed, filtered, and transferred to HT1080 cells. Polybrene is added to a final concentration of 4ug/ml. On day 4, medium on the HT1080cells is replaced with fresh DMEM containing 10% Fetal Calf Serum, and 100 mg/ml hygromycin. Selection is continued on days 5 through 20 until hygromycin resistant colonies can be counted, and all negative controls (e.g., mock infected MdH cells) are dead.

Example 7

Production of Extended VPCL Cell Cultures for Stability Testing

Figure 7A:
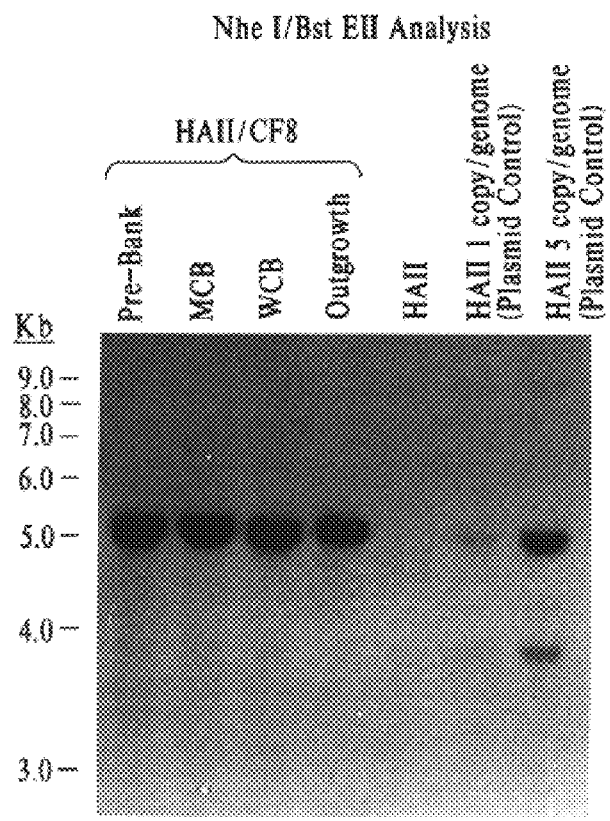
FIGS. 7A and 7B are Southern Blots of provector structure.

This example describes the generation of high titer VPCL clone banks at various times after completion of VPCL clone production for the purpose of stability testing. The four banks are called Pre-bank, Master Cell Bank (MCB), Working Cell Bank (WCB) and "Outgrowth" for extended cell cultures. The four banks are characterized regarding the stability of the retroviral components gag/pol, env and vector as well as titer production and RCR occurrence (FIGS. 7–9).

The VPCL Pre-bank is generally produced and frozen 2–3 months post-transduction. A vial of the Pre-bank is thawed and 2–3 weeks later a MCB is generated and frozen under GLP conditions. Then, one vial of the MCB is thawed and 2–3 weeks later a WCB is generated and frozen under GLP conditions. To produce the "Outgrowth", one vial of the WCB is thawed, cultured for approximately 6 weeks and then the "Outgrowth" bank is frozen.

Example 8

Figure 2:
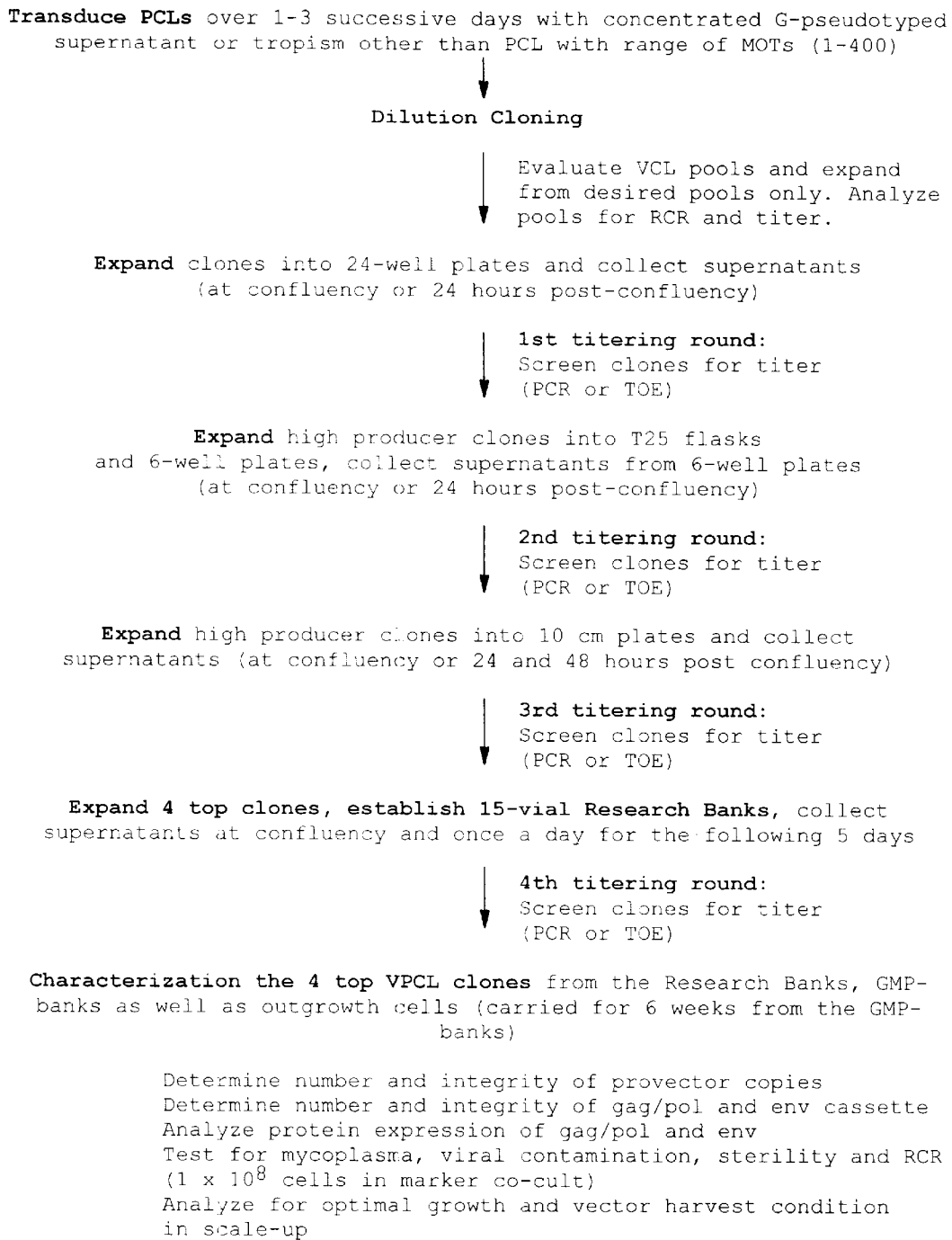
FIG. 2 schematically illustrates one representative strategy for the production and selection of high titer retroviral vector particle producing cell lines.

Production of High Titer Retroviral Producer Pools and Clones Using the High Mot Approach This example describes the production of high titer producer pools and clones using a transduction method that will lead to very high viral particle output through stable integration of more than one copy of retroviral provectors per genome. This process is called the "high mot approach", preferably using multiplicities of transductions (mot) of $\geq 20$. The generality of this approach is shown by the Examples described below and the general strategy for high titer VPCL production is outlined in FIG. 2.

In this example the production of producer pools and clones is described using a number of various transgenes and PCLs. First, for proof of principle, the PCLs DA, HA, HX, 2A and 2X were used for the production of high titer pools and clones (see Example 8A–B). Then the high mot approach was applied toward the production of VPCL pools and clones derived from the next generation human PCLs HA-LB, HAII and 2A-LB (see Example 8C–E) which are "cross-less" and therefore have reduced RCR risk.

A. Production of HX/GH827 Producer Pools and Clones

This example describes the generation of high titer retroviral VPCL pools and clones which produce viral particles coding for the human growth hormone gene. HX PCL cells were seeded at $3.7 \times 10^5$ cells/well of a 6-well plate and transduced 24 h later with concentrated and purified amphotropic vector from the canine producer cell line DA/GH827. The retroviral vector GH827 which codes for hGH and the neo$^r$ gene (Example 1A). The multiplicities of transduction were 0.1, 0.5, 5, 25 and 125. The five resulting transduced pools were selected with 0.6 mg G418/ml until untransduced control cells were dead. The five pools were named HX/GH827 0.1, -0.5, -5, -25 and -125.

For production of VPCL clones, the pools HX/GH827 0.1 and -25 were dilution cloned using standard procedures and 24 VPCL clones per pool isolated. The analysis of these VPCL pools and some clones is described in Example 9A (Tables 3 and 4).

B. Production of HX-, 2X-, DA- and 2A/CBb-gal Producer Pools and Clones

To further examine the generality of the high mot approach resulting in higher titer VPCLs, a retroviral vector with a different gene of interests was introduced into 4 PCLs applying a wide range of multiplicities of transduction. Retroviral vector CBb-gal codes for the b-galactosidase and the neo$^r$ n gene (Example 1B). Amphotropic CBb-gal vector derived from a canine DA/CBb-gal VPCL and xenotropic CBb-gal vector derived from a 2X/CBb-gal VPCL clone were concentrated and purified similar to methods described in Example 5. The b-galactosidase titers of both concentrated vectors were determined using the x-gal stain procedure described in Example 3A-2.

Due to the phenomenon of "receptor blocking", the xenotropic PCLs HX and 2X were transduced with the amphotropic DA/CBb-gal vector and the amphotropic PCLs DA and 2A were transduced with the xenotropic 2X/CBb-gal vector. The range of mot for each PCL was 0.1, 0.5, 5, 25 and 125. The resulting 20 pools were selected with the antibiotic G418 until untransduced control cells were dead. G418 concentrations for the selection were as follows: 0.4 mg/ml for the 2X/CBb-gal and 2A/CBb-gal pools, 0.6 mg/ml for the DA/CBb-gal pools and 0.8 mg/ml for the HX/CBb-gal pools (FIG. 3).

Figure 4A:
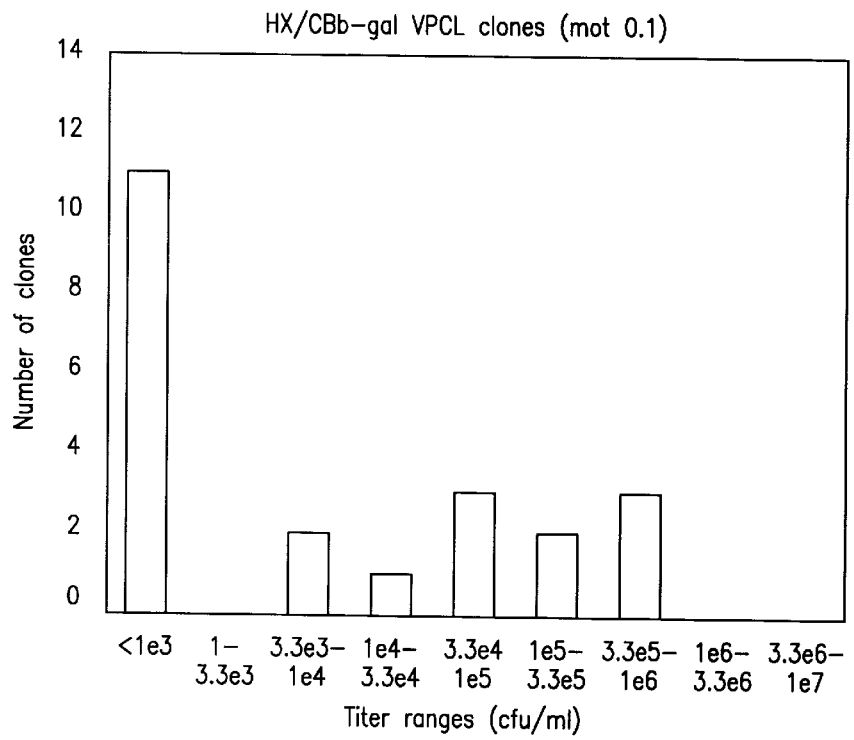
FIGS. 4A and 4B are bar graphs which show titer data from randomly selected VPCL clones.
Figure 4B:
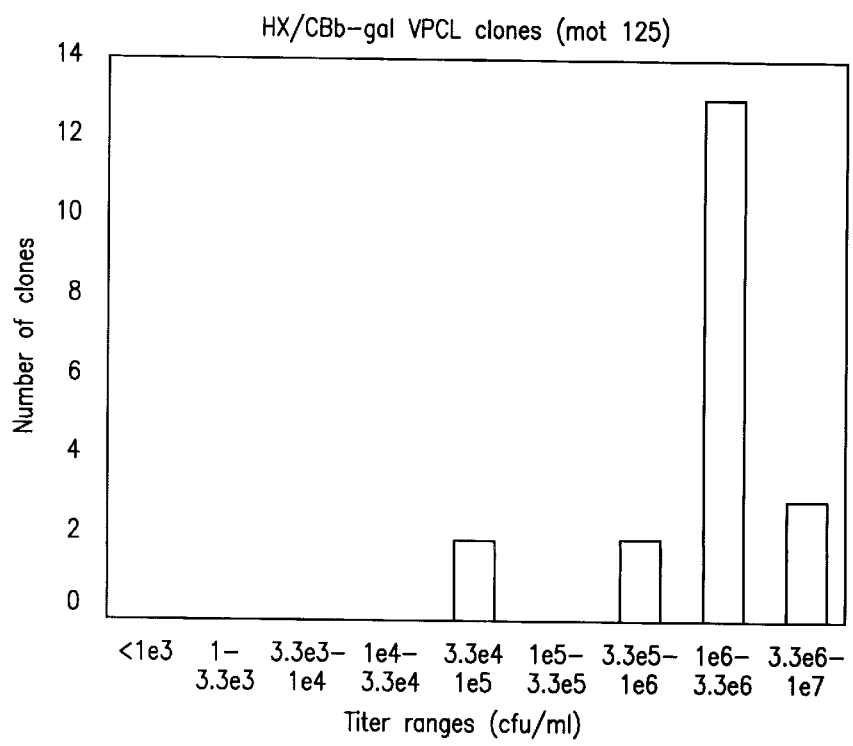
Figure 5A:
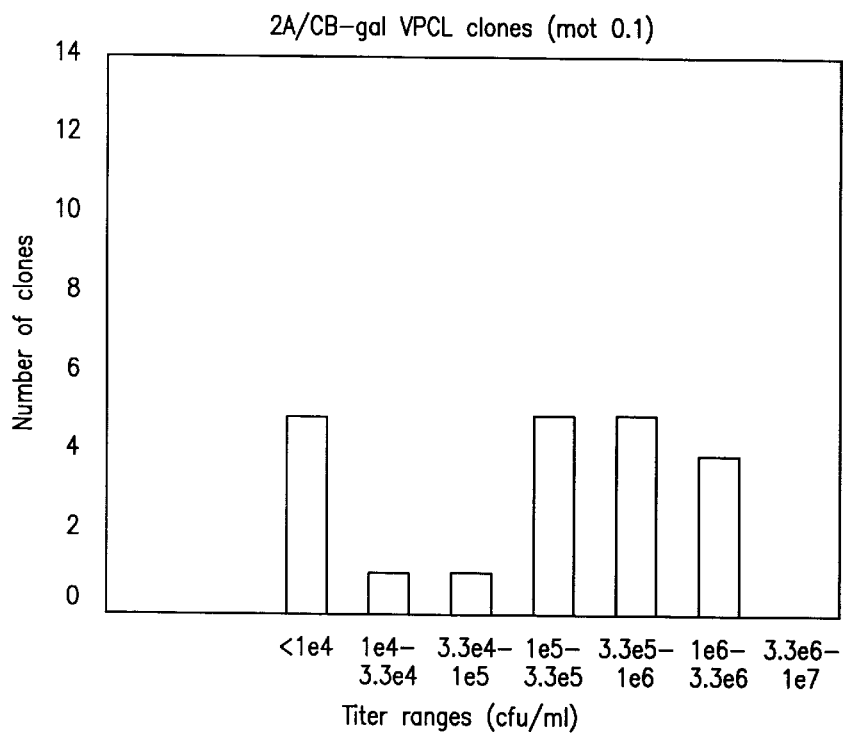
FIGS. 5A and 5B are bar graphs which show titer data from randomly selected VPCL clones.
Figure 5B:
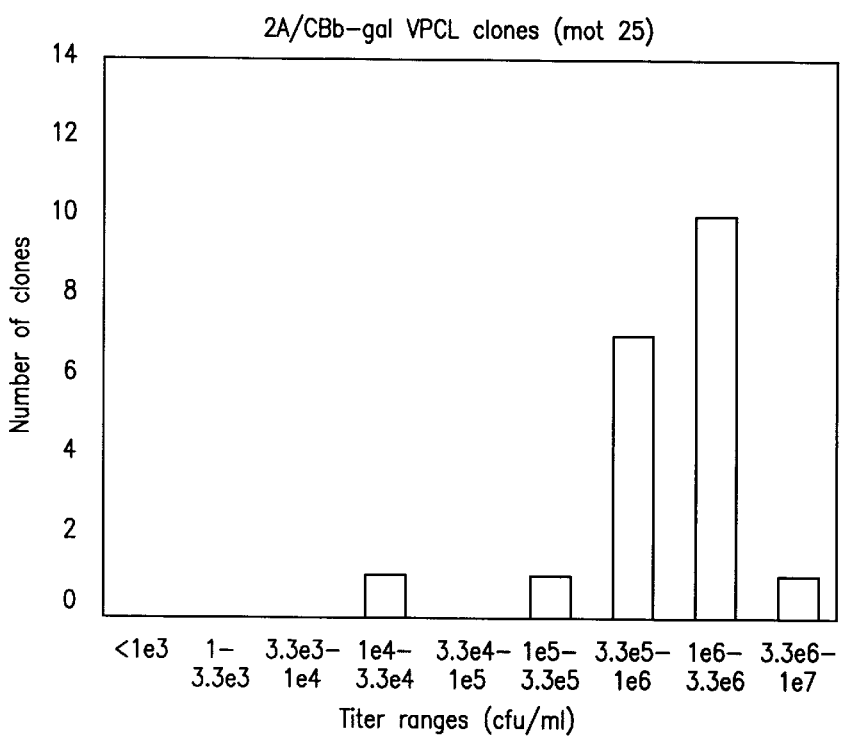

To investigate whether increased titer of VPCL produced by high mot correlates with increased provector copy number, four producer pools were dilution cloned since only single cell clones allow the analysis of provector copy number via Southern blot. Two VPCL pools with low titer (2A/CBb-gal mot 0.1, HX/CBb-gal mot 0.1) as well as two pools with high titer (pools 2A/CBb-gal mot 25, HX/CBb-gal mot 125) were chosen. The four b-galactosidase VPCL pools were dilution cloned in 96-well plates following standard procedures and clones randomly chosen. A total of 22 VPCL clones for HX/CBb-gal mot 0.1, 20 clones for HX/CBb-gal mot 125, 21 clones for 2A/CBb-gal mot 0.1 and 20 clones for 2A/b-gal mot 25 were isolated. The analysis of these 4 VPCL pools and 83 clones is described in Example 9B (FIGS. 4 and 5).

C. Production of HAII-, HA-LB- and 2A-LB/hFVIII Producer Pools and Clones

This example describes the generation of high titer retroviral VPCL pools and clones which produce viral particles coding for a truncated form of the human factor VIII gene. Transient VSV-G supernatant was produced and concentrated using the pCF8 retroviral vector (Example 1C) and the 2A-LB PCL as described in Examples 4 and 5. The titer of the VSV-G supernatant was $1 \times 10^7$ cfu/ml as determined by the hFVIII TOE and the PCR titer assays. This VSV-G pseudotyped vector preparation was used to transduce the three human PCLs with reduced RCR potential, 2A-LB, HA-II and HA-LB (Example 2). Three sets of VPCL pool and clone production were carried out using the retroviral vector pCF8 and one or two of the PCLs HAII, HA-LB and 2A-LB.

C-1. Set I: 2A-LB/hFVIII and HAII/hFVIII VPCL Pools and Clones, Mot 10–200

Figure 6A:
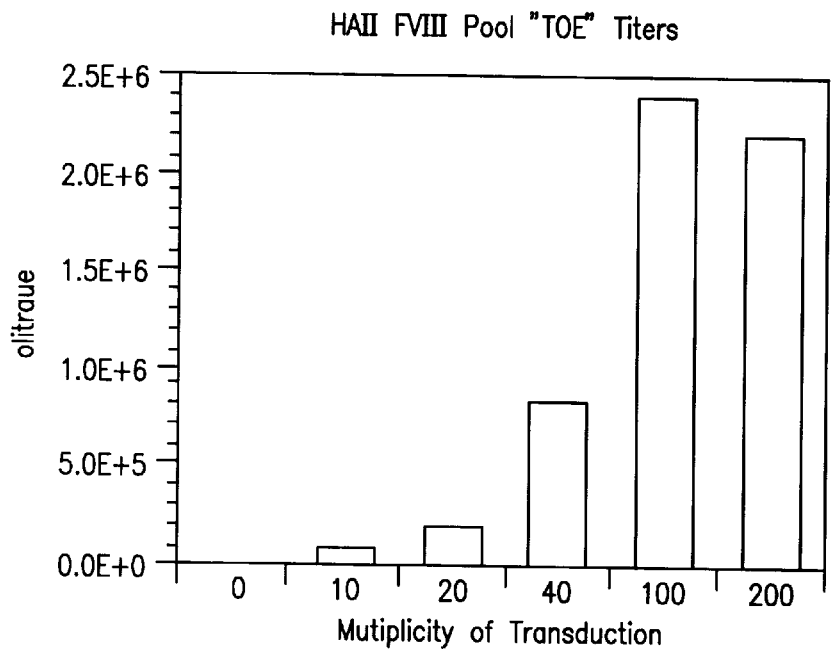
FIGS. 6A and 6B are bar graphs which show titer data from HAII/hfVIII VPCL pools produced at range of multiplicity of transduction.
Figure 6B:
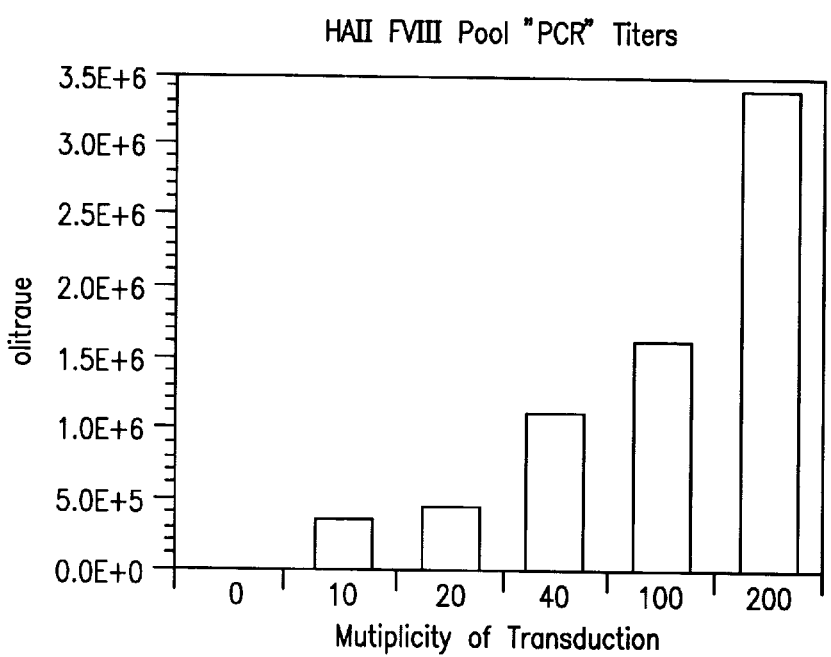

For the generation of 2A-LB/hFVIII and HA-II/hFVIII VPCL pools, 2A-LB and HAII PCL cells were plated at $5\times10^4$ cells/well (6-well plates) and transduced at mots of 10, 20, 40, 100 and 200. The transduction volume was in a total of 1.5 ml and incubated overnight at 37° C. On day two, the VSV-G supernatant was replaced with the same volume of fresh VSV-G supernatant and again placed at 37° C. overnight. This procedure was repeated for a third time, so that the overall transduction procedure was carried out over three successive days. To evaluate each VPCL pool while minimizing any potential toxic effects of the transduction process, the transduced PCLs were allowed to grow to confluency, the VPCL pools harvested and replated at 0.5 or $1\times10^6$ cells/well (in 6-well plates). Results of the analysis of the 2A-LB/hFVIII and HAII/hFVIII VPCL pools are described in Example 9C-1 (FIG. 6).

In order to analyze 2A-LB/hFVIII and HAII/hFVIII VPCL clones, a total of six 2A-LB and HAII VPCL pools, transduced at mots of 40 and 100, were dilution cloned into 96-well plates according to standard procedures. A total of 527 VPCL clones were subjected to three separate rounds of TOE titer screening resulting in the selection of 13 high titer VPCL clones as summarized in Example 9C- 1, Table 7.

C-2. Set II: HA-LB/hFVIII VPCL Pools and Clones, Mot 10–100

For the generation of HA-LB/hFVIII VPCLs, HA-LB PCLs were plated at 1 or $2\times10^5$ cells/well and transduced at mots of 10, 20, 40, 100 for three or two successive days, respectively. All eight pools were produced as described in Example 8C-1, cells grown to confluency, replated at the same density and supernatant collected for analysis summarized in Example 9C-2.

In order to analyze HA-LB/hFVIII VPCL clones, each of the 8 transduced pools were dilution cloned in 96-well plates and 48 randomly chosen clones from each pool expanded and subjected to three rounds of screening to identify the highest titer clones. A total of 384 producer clones were screened which resulted in the production of 10 high titer VPCL clones as summarized by Table 11 of Example 9C-2.

C-3. Set III: HA-LB/hFVIII VPCL Pools and Clones, Mot 0.1–125

In order to compare the effects of the full range of mot on titer, HA-LB was transduced with concentrated hFVIII/VSV-G supernatant at mot's of 0.1, 0.5, 5, 25 and 125. This range of mot is identical to the one described in Example 8A and B. For the generation of HA-LB/hFVIII VPCLs, HA-LB PCLs were plated at $1\times10$ cells/well (6-well plate) and transduced at above mentioned mots for one day. All 5 pools were grown to confluency, replated at the same density and supernatant collected for analysis summarized in Example 9C-3 (Table 12).

Figure 12:
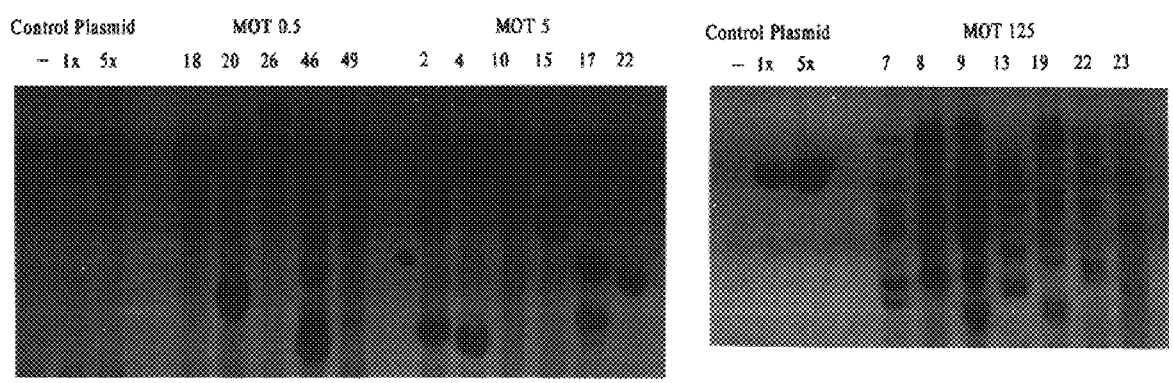
FIG. 12 is a Southern blot analysis of HA-LB/hfVIII VPCL clones derived from several different multiplicity of transduction pools.

In order to analyze HA-LB/hFVIII VPCL clones, the mot 0.1, 5 and 125 pools were dilution cloned in 96-well plates, clones randomly chosen from each pool and analyzed as described in Example 9C-3 (Table 13, FIG. 12).

D. Production of 2A-LB/IL-4 Producer Pools and Clones

This example describes the generation of high titer retroviral VPCL pools and clones which produce viral particles coding for the rat interleukin-4 gene. Concentrated rIL-4/VSV-G supernatant was produced and concentrated using the pBA-9b/rIL-4 retroviral vector (Example 1D) and the 2A-LB PCL as described in Examples 4 and 5. The PCR titer of the rIL-4/VSV-G supernatant was determined as described in Example 3B and gave $1\times10^7$ cfu/ml. This supernatant was used to transduce the 2A-LB PCL which was plated at low density (LD) of $5\times10^4$ or high density (HD) of $2.5\times10^5$ cells/well (6-well plates). Transductions were carried out for three successive days at mots of 1, 5, 10, 25, 50 and 125 in a total volume of 1.5 ml as described in Example 8C. Pools were initially evaluated for rIL-4 protein expression levels using the ELISA capture assay described in Example 3A-4.

In order to analyze 2A-LB/rIL-4 VPCL clones, the four pools with the highest rIL-4 expression (LD mot 25, HD mot 10, HD mot 25, HD mot 50) were dilution cloned in 96-well plates and between 35 and 54 randomly chosen clones from each pool expanded and subjected to three rounds of screening using the ELISA capture assay. Results from the analysis of 2A-LB/rIL-4 VPCL pools and clones are described in Example 9D.

E. Production of HA-LB/eGFP Producer Pools

This example describes the generation of high titer retroviral VPCL pools which produce viral particles coding for the enhanced green fluorescence protein. Concentrated eGFP/VSV-G supernatant was produced and concentrated using the pBA-9b/eGFP retroviral vector (Example 1E) and the 2A-LB PCL as described in Examples 4 and 5. The PCR titer of the eGFP/VSV-G supernatant was determined as described in Example 3B and gave $1\times10^8$ cfu/ml. This supernatant was used to transduce the PCL HA-LB only once at mots of 9, 19, 37.5, 75, 150 and 300. To evaluate each VPCL pool while minimizing any potential toxic effects of the transduction process, the transduced PCLs were allowed to grow to confluency, the VPCL pools harvested and replated at 0.5 or $1\times10^6$ cells/well (in 6-well plates). The 6 resulting HA-LB/eGFP VPCL pools did not undergo dilution cloning and were analyzed as described in Example 9E (Table 15).

Example 9

Analysis of Retroviral Producer Pools and Clones Generated Via the High Mot Approach The retroviral producer pools and clones were analyzed to varying degrees for titer, number of integrated provectors per genome, RCR generation as well as stability testing. We conclude, that, during VPCL production, an increase of mot within a certain range leads to a titer increase which generally correlates with an increased number of provector copies and expression level of genomic vector RNA. The mot for optimal titer production varies from PCL and retroviral vector used for VPCL production and needs to be determined for each particular combination. The high mot approach process assures that the optimum provector number is determined and VPCL clones be derived from pools with the highest titer only.

A. Analysis of HX/GH827 Producer Pools and Clones

This example describes the TOE titer analysis of the 5 producer pools HX/GH827 0.1, -0.5, -5, -25 and -125 as well as derived 48 clones (see Example 8A). All 5 VPCL pools were seeded at the same cell density, supernatant harvested at confluency, filtered (0.45 um) and the neo$^r$ titer determined as described in Example 2A-5. The neo$^r$ titer values are shown in Table 3 and indicate a titer increase of at least 7-fold from the VPCL pool produced at mot 0.1 to the pool produced at mot 25 pool. This increase is followed by a small decline at the mot 125 pool.

TABLE 3

Neo$^r$ titer of HX/GH827 VPCL pools produced
at a range of mot from 0.1 to 125

| VPCL pool | Pools produced with mot of | Neo$^r$ titer in pools (cfu/ml) |
|---|---|---|
| HX/GH827 0.1 | 0.1 | 0.9 × 10$^6$ |
| HX/GH827 0.5 | 0.5 | 1.2 × 10$^6$ |
| HX/GH827 5 | 5 | 4.2 × 10$^6$ |
| HX/GH827 25 | 25 | 7.4 × 10$^6$ |
| HX/GH827 125 | 125 | 6.0 × 10$^6$ |

The 24 VPCL clones each from the low titer pool HX/GH827 0.1 and the high titer pool HX/GH827 25 were plated at the same density, supernatants harvested, filtered (0.45 um). Supernatants used to transduce target cells and resulting supernatants analyzed for hGH expression levels as described in Example 3A-3 (data not shown). The supernatant from the six VPCL clones with the highest hGH levels from each of the two pools were harvested, filtered (0.45 um) and used to determine the neo$^r$ titer as described in Example 3A-5. The results are shown in Table 4 below and indicate that the average titer of the top VPCL clones derived from the mot 25 pool are at least 10-fold higher than the clones derived from the mot 0.1 pool.

TABLE 4

Neo$^r$ titer of HX/GH827 VPCL clones derived from
pools produced at mot 0.5 or mot 25

| VPCL Clones | Neo$^r$ titer (cfu/ml) |
|---|---|
| Clones derived from 0.5 mot pool | |
| HX/GH827 0.5 #8 | 0.3 × 10$^6$ |
| HX/GH827 0.5 #9 | 0.4 × 10$^6$ |
| HX/GH827 0.5 #10 | 1.3 × 10$^6$ |
| HX/GH827 0.5 #18 | 0.4 × 10$^6$ |
| HX/GH827 0.5 #21 | 1.7 × 10$^6$ |
| HX/GH827 0.5 #23 | 0.5 × 10$^6$ |
| | Average titer: 0.8 × 10$^6$ |
| Clones derived from 25 mot pool | |
| HX/GH827 25 #9 | 0.43 × 10$^7$ |
| HX/GH827 25 #11 | 1.10 × 10$^7$ |
| HX/GH827 25 #12 | 0.23 × 10$^7$ |
| HX/GH827 25 #15 | 0.30 × 10$^7$ |
| HX/GH827 25 #17 | 1.80 × 10$^7$ |
| HX/GH827 25 #19 | 2.5 × 10$^7$ |
| | Average titer: 1.1 × 10$^7$ |

B. Analysis of HX-, 2X-, DA- and 2A/CBb-gal Producer Pools and Clones

This example summarizes the analysis of the 20 VPCL producer pools and 83 VPCL clones described in Example 8B and includes titer and provector copy number analyses.

B-1. b-galactosidase Titer of VPCL Pools

The b-galactosidase titers of the 20 selected producer pools HX/CBb-gal (mot 0.1–125), 2X/CBb-gal (mot 0.1–125), DA/CBb-gal (mot 0.1–125) and 2A/CBb-gal (mot 0.1–125) were determined in triplicates using the Galacto-Light titer assay (described in Example 3A-2). The 20 VPCL pools were seeded at an equal cell density, supernatant was harvested at 100% confluency, filtered (0.45 um) and used to transduce the HT-1080 target cells for b-galactosidase titer determination.

Titer results from the 20 VPCL pools are shown in FIG. 3 and indicate that depending on the combination of the retroviral vector and PCL, the effects of the high mot approach on titer are more or less pronounced. In general though, the benefit of the high mot approach can be significant as demonstrated by the titer increase of nearly 100-fold comparing the HX/CBb-gal VPCL low and high mot pools.

B-2. b-galactosidase Titer of VPCL Clones

The b-galactosidase titers of VPCL clones derived from the low mot transductions 2A/CBb-gal mot 0.1 (21 clones) and HX/CBb-gal mot 0.1 (22 clones) as well as high mot transductions 2A/CBb-gal mot 125 (20 clones) and HX/CBb-gal mot 25 (20 clones) were determined in triplicates using the Galacto-Light titer assay (see Example 3A-2). All VPCL clones were seeded at equal densities, supernatant harvested, filtered (0.45 um) and supernatants used to transduce HT-1080 target cells for titer determination. The titer results are shown in FIGS. 4 and 5. Approximately 50% of the VPCL clones derived from the HX/CBb-gal mot 0.1 pool have a titer lower than 1×10$^3$ cfu/ml whereas the VPCL clones derived from the HX/CBb-gal mot 125 pool have an average titer of 1×10$^6$ cfu/ml (FIG. 4). The average titer of the VPCL clones derived from the 2A/CBb-gal mot 0.1 pool is approximately 10-fold lower than the clones derived from the 2A/CBb-gal mot 25 pool (FIG. 5).

B-3. Analysis of Retroviral Provector Copy Number

To elucidate whether the differences in titer between the VPCL clones derived from low vs high mot pools was related to the number of provector copies that stably integrated into the genome, a Southern blot analysis was carried out to determine the provector copy number in VPCL clones. Genomic DNA was isolated from VPCL clones using Qiagen's genomic DNA isolation kits and procedures (Qiagen Inc., Chatsworth, Calif.). The genomic DNA was digested such that a single band in a Southern blot represents one provector. The Southern blot analysis was carried out using standard procedures and a b-galactosidase-specific DNA probe derived from the retroviral vector pCBb-gal used for detection.

Five VPCL clones with representative titers derived from the HX/b-gal 0.1, HX/b-gal 125, 2A/b-gal 0.1 and 2A/b-gal 25 pools each (see Example 8B) were analyzed in the Southern blot. The b-galactosidase titer values and the number of provector copies per genome of these particular VPCL clones are shown in Table 5 below. The results indicate that there is a strong correlation between titer and provector copy number.

TABLE 5 b-galactosidase titers and provector copy number
in VPCL clones derived from pools with low and high mots

| VPCL clones | b-galactosidase titer in cfu/ml | Provector copy number |
|---|---|---|
| HX/CBb-gal mot 0.1 | | |
| #11 | 5.6 × 10$^3$ | 1 |
| #18 | 1.6 × 10$^4$ | 1 |
| #16 | 7.2 × 10$^3$ | n.d. |
| #12 | 3.7 × 10$^4$ | 1 |
| #22 | <1.0 × 10$^3$ | 1 |
| HX/CBb-gal mot 125 | | |
| #19 | 1.3 × 10$^6$ | 4–7$^a$ |
| #20 | 1.6 × 10$^6$ | 7–8$^a$ |
| #7 | 2.1 × 10$^6$ | 7–10$^a$ |
| #1 | 2.5 × 10$^6$ | 6 |
| #11 | 2.5 × 10$^6$ | 7–8$^a$ |
| 2A/CBb-gal mot 0.1 | | |
| #4 | 1.1 × 10$^5$ | 1 |
| #5 | 1.2 × 10$^5$ | 2 |

TABLE 5-continued b-galactosidase titers and provector copy number
in VPCL clones derived from pools with low and high mots

| VPCL clones | b-galactosidase titer in cfu/ml | Provector copy number |
|---|---|---|
| #12 | $3.2 \times 10^5$ | 4 |
| #19 | $1.0 \times 10^5$ | 2 |
| #21 | $1.4 \times 10^5$ | 7–8[a] |
| 2A/CBb-gal mot 25 | | |
| #6 | $8.9 \times 10^5$ | 8–10[a] |
| #17 | $7.1 \times 10^5$ | 8 |
| #14 | $1.0 \times 10^6$ | 8–10[a] |
| #5 | $1.1 \times 10^6$ | 4 |
| #20 | $1.3 \times 10^6$ | 6–8[a] | n.d. = not determined
[a]Numbers of integrated proviral copies could not be determined more accurately due to overlapping bands in Southern blots C. Analysis of HAII-, HA-LB- and 2A-LB/hFVIII Producer Pools and Clones This example summarizes the analysis of the three sets of hfVIII VPCL pools and clones produced at mots of 0.1–200 as described in Example 8C. The summary includes titer, retroviral provector copy number, RCR analysis and stability testing.

C-1. Analysis of Set I: 2A-LB/hFVIII and HAII/hFVIII VPCL Pools and Clones, Mot 10–200

A titer analysis on supernatant from the VPCL producer pools 2A-LB/hfVIII and HA-II/hFVIII, both generated at mots of 10, 20, 40, 100 and 200, was carried out as described in Example 3A-3 and 3B. VPCL pools were allowed to grow to confluency, after which they were replated at a constant cell number (0.5 or $1 \times 10^6$/well, 6-well) and again grown to confluency, fresh media added, supernatants collected and filtered (0.45 um) at multiple days post-confluency. 30, 100 and 300 ul volumes of each supernatant was used in the hFVIII TOE assay and PCR titers determined where specified. Titer results are shown in Table 6 and FIG. 6. There is a clear correlation between increases in pool titers and mot with a minimum increase in titer of 10-fold up to a maximum increase of 28-fold between mot 10 and mot 200 pools. Furthermore, Table 6 indicates that the PCR and the hFVIII TOE titer are fairly comparable.

TABLE 6

TOE and PCR titer analysis of 2A-LB/hFVIII and
HAII/hFVIII pools produced at an mot range of 10–200

| Mot | 2A-LB/FVIII confluent TOE | 2A-LB/FVIII confluent PCR | 2A-LB/FVIII 24 h post-confluent, TOE | HAII/FVIII confluent TOE | HAII/FVIII confluent PCR | HAII/FVIII 24 h Post-confluent, TOE |
|---|---|---|---|---|---|---|
| 10 | $5.3 \times 10^4$ | $8.7 \times 10^4$ | $4.5 \times 10^4$ | $5.4 \times 10^4$ | $3.7 \times 10^5$ | $7.8 \times 10^4$ |
| 20 | $6.1 \times 10^4$ | $1.6 \times 10^5$ | $5.1 \times 10^4$ | $1.3 \times 10^5$ | $4.5 \times 10^5$ | $1.8 \times 10^5$ |
| 40 | $2.1 \times 10^5$ | $2.2 \times 10^5$ | $1.4 \times 10^5$ | $7.5 \times 10^5$ | $1.1 \times 10^6$ | $8.3 \times 10^5$ |
| 100 | n.d. | n.d. | n.d. | $1.7 \times 10^6$ | $1.6 \times 10^6$ | $2.4 \times 10^6$ |
| 200 | $9.0 \times 10^5$ | $9.6 \times 10^5$ | $1.1 \times 10^6$ | $1.5 \times 10^6$ | $3.4 \times 10^6$ | $2.2 \times 10^6$ | n.d. = not determined

VPCL clones were produced from the 2A-LB/hFVIII mot 40 and mot 100 as well as from the HAII/hFVIII mot 40 and 100 pools and dilution cloning carried out in 96-well plates using standard procedures. Table 7 below describes the VPCL production process in the context of screening procedures used and numbers of hfVIII producer clones tested. Each round of screening set a higher criterion for the titer resulting in a final number of 13 high titer VPCL clones (titer results shown in Table 8).

TABLE 7

Summary of screening strategy for 2A-LB and
HAII/hFVIII VPCL clones

| | 1st round | 2nd round | 3rd round |
|---|---|---|---|
| Number clones screened | 527 | 50 | 29 |
| Number positive clones | 47% | 100% | 100% |
| Criterion TOE titer for expansion (cfu/ml) | $2–4 \times 10^5$ | $2 \times 10^6$ | $4 \times 10^6$ (2A-LB) $9 \times 10^6$ (HAII) |

TABLE 8 hFVIII TOE and PCR titer of 24-hour post-confluent supernatants
from hFVIII VPCL clones derived from 2A-LB and HAII PCLs
transduced with mots of 40 and 100

| VPCL | Clone derived from pools transduced with mot | TOE titer (cfu/ml) | PCR titer (cfu/ml) |
|---|---|---|---|
| 2A-LB/hFVIII #61 | 40 | $9.3 \times 10^6$ | $1.1 \times 10^7$ |
| 2A-LB/hFVIII #92 | 40 | $7.3 \times 10^6$ | $9.7 \times 10^6$ |
| 2A-LB/hFVIII #172 | 40 | $4.2 \times 10^6$ | $9.6 \times 10^6$ |
| 2A-LB/hFVIII #25 | 100 | $4.4 \times 10^6$ | $5.4 \times 10^6$ |
| 2A-LB/hFVIII #62 | 100 | $4.8 \times 10^6$ | $5.2 \times 10^6$ |
| HAII/hFVIII #7 | 40 | $9.0 \times 10^6$ | $1.0 \times 10^7$ |
| HAII/hFVIII #55 | 100 | $1.5 \times 10^6$ | $4.1 \times 10^6$ |
| HAII/hFVIII #56 | 100 | $1.8 \times 10^6$ | $4.3 \times 10^6$ |
| HAII/hFVIII #67 | 100 | $2.3 \times 10^6$ | $4.6 \times 10^6$ |
| HAII/hFVIII #11 | 100 | $5.6 \times 10^6$ | $1.0 \times 10^7$ |
| HAII/hFVIII #52 | 100 | $5.7 \times 10^6$ | $7.2 \times 10^6$ |
| HAII/hFVIII #53 | 100 | $5.3 \times 10^6$ | $1.2 \times 10^7$ |
| HAII/hFVIII #66 | 100 | $9.6 \times 10^6$ | $1.6 \times 10^7$ |

The potential "static" titer for top VPCL clones 2A-LB/hFVIII#61 and -172 as well as HAII/hFVIII#11 derived from the human PCLs 2A-LB and HAII with reduced RCR potential is $0.5–1.0 \times 10^7$, and $2.0 \times 10^7$ cfu/ml, respectively.

The RCR analysis for the VPCL clones 2A-LB/hFVIII#61, -92, -172 and HAII/hFVIII#7, -11, -53 and -66 was carried out as described in Example 6 and all VPCL clones were found to be free of RCR.

Extensive stability testing was carried out on the HAII/hFVIII#11 VPCL clone (see Table 8). The four banks (Pre-bank, MCB, WCB, "Outgrowth") were generated as described in Example 7. The total culture time of HAII/hFVIII#11 after transduction is 10 weeks for the Pre-bank, 13 weeks for the MCB, 16 weeks for the WCB and 21 weeks for the "Outgrowth". The four banks for the VPCL clone were tested for stability of the retroviral components gag/pol, env and vector, the clone titer and RCR testing.

RCR testing was carried out on all four VPCL banks as described in Example 6 and all banks were found to be free of detectable RCR.

Human FVIII TOE and PCR titer analysis was carried out on all four VPCL banks as described in Example 3 and the results shown in Table 9 indicate that all titers from all four banks are very similar.

TABLE 9 hFVIII TOE and PCR of the four HAII/hFVIII banks

| HAII/hFVIII banks | TOE titer (cfu/ml) | PCR titer (cfu/ml) |
|---|---|---|
| Pre-bank | $1.1 \times 10^7$ | $7.4 \times 10^6$ |
| MCB | $1.1 \times 10^7$ | $6.6 \times 10^6$ |
| WCB | $1.1 \times 10^7$ | $1.2 \times 10^7$ |
| "Outgrowth" | $1.1 \times 10^7$ | $1.1 \times 10^7$ |

To examine the stability of the provector in the HAII/CF8 VPCL over time, Southern blot experiments of DNA prepared from HAII/hFVIII cultures derived from the Pre-Bank, MCB, WCB, and "Outgrowth" was digested with either BglII or NheI and BstEII were performed using standard procedures. Restriction enzyme analysis with NheI and BstEII, each of which cut once within regions flanking the hFVIII gene, gave rise to the expected 5.2 Kb band for the integrated pCF8 provector. The Southern Blot in FIG. 7A verifies that the correct size of the integrated provector as well as copy numbers are maintained throughout HAII/hFVIII VPCL from the Pre-Bank to the Outgrowth cells.

Figure 7B:
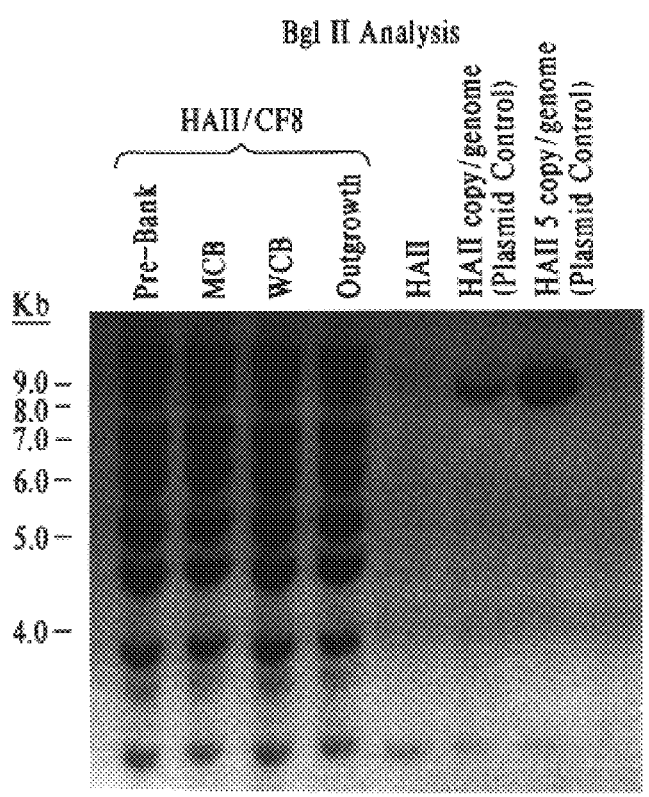

BglII cuts once within the provector structure and at the adjacent sites in the host cell DNA. Southern analysis on BglII-digested genomic DNA provides a "finger print" of the vector integration site with the number of bands hybridizing to the hFVIII probe indicative of the total number of integrated provectors. The results in FIG. 7B show the presence of 6 bands of equal intensity ranging in size between 3.8, and approximately 15 Kb. The Southern blots in FIG. 7 show the identical pattern of bands for HAII/hFVIII at all the stages of cell banking and expansion indicating stability of the size and number of integrated sites of the provector sequences.

Figure 8A:
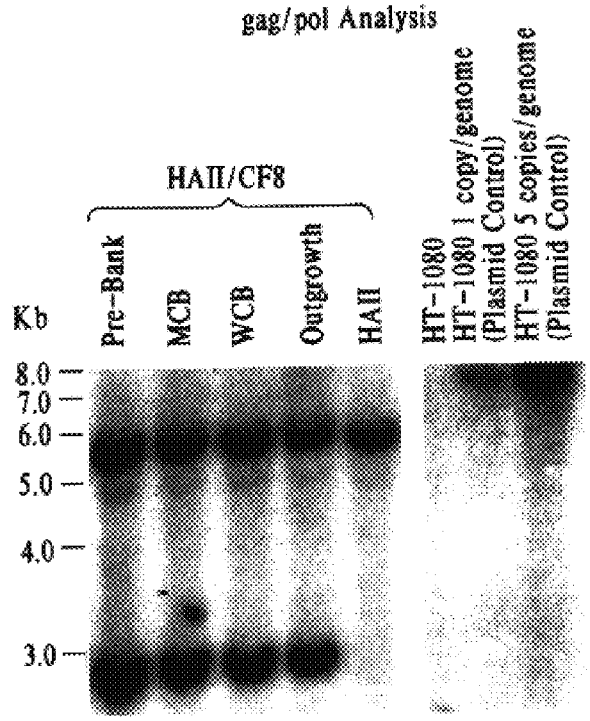
FIGS. 8A and 8B are Southern Blots of MLV structural genes of four banks from HAII/hfVIII VPCL.
Figure 8B:
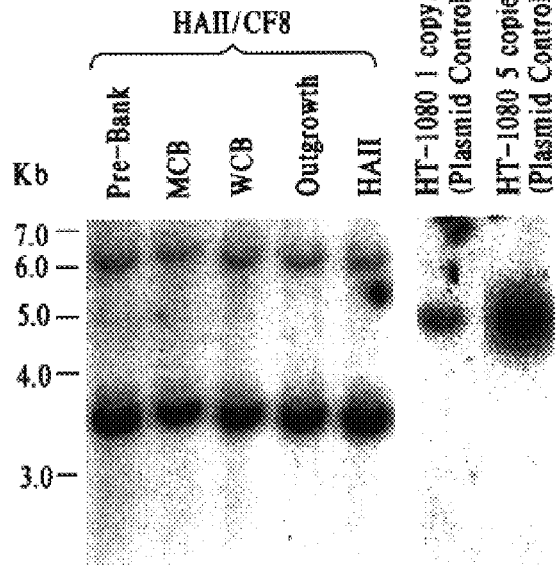
Figure 9:
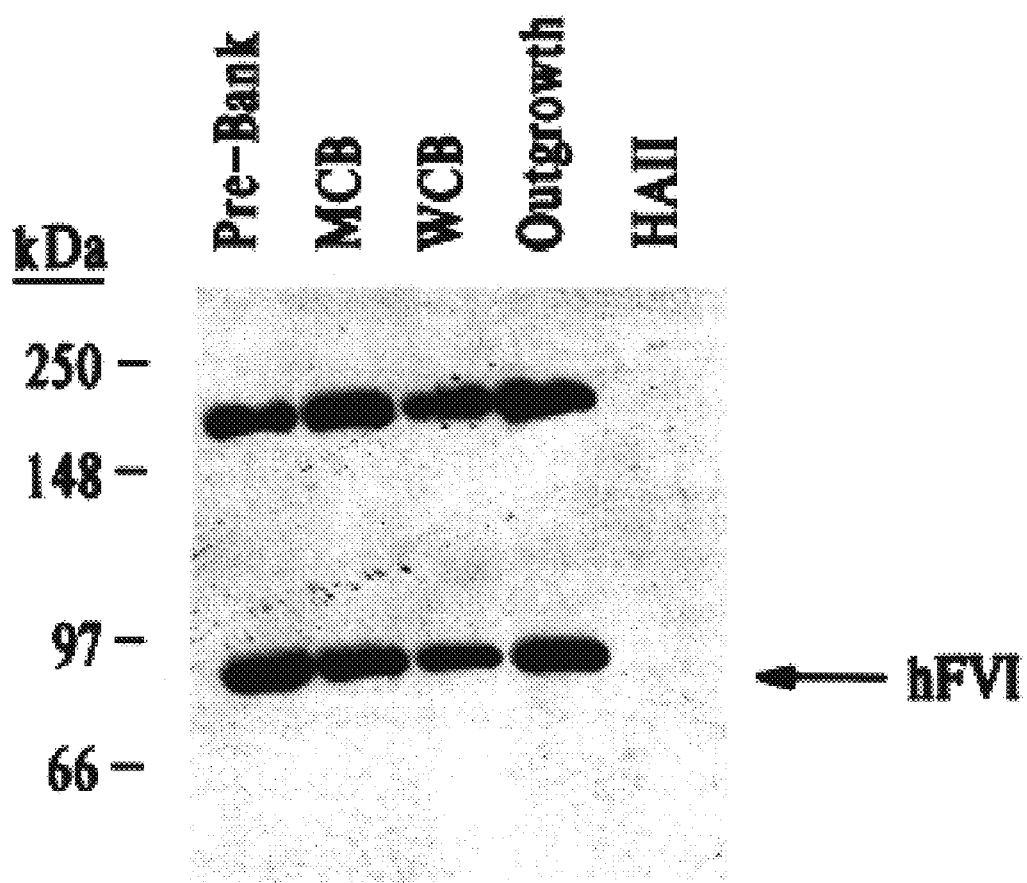
FIG. 9 is a Western Blot analysis of four banks from HAII/hFVIII VPCL.

The stability of the MLV structural and enzymatic genes gag/pol and env was investigated by Southern blots of the VPCL HAII/hFVIII Pre-bank, MCB, WCB and "Outgrowth" (FIG. 8). The pattern of the env bands are indistinguishable between the PCL HAII and all four banks of HAII/hFVIII both in apparent molecular weight and intensity (FIG. 8B). The number of gag/pol between the VPCL HAII/hFVIII Pre-Bank, MCB, WCB, and "Outgrowth" is identical (FIG. 8A).

The hfVIII protein expression of the pCF8 provector gene in the four banks of HAII/hFVIII were investigated. Briefly, to determine hfVIII protein expression, intracellular lysates were prepared from HAII/hFVIII cells expanded from the Pre-Bank, MCB, WCB, and "Outgrowth". The lysates were analyzed by Western blot using antibodies directed against the light chain of the hFVIII protein using standard procedures. Western blots of lysates from all stages of HAII/hFVIII VPCL development consistently showed the presence of the 80 kDa light chain and the 185 kDa unprocessed hFVIII protein (FIG. 9).

C-2. Analysis of Set II: HA-LB/hFVIII VPCL Pools and Clones, Mot 10–100

Figure 10:
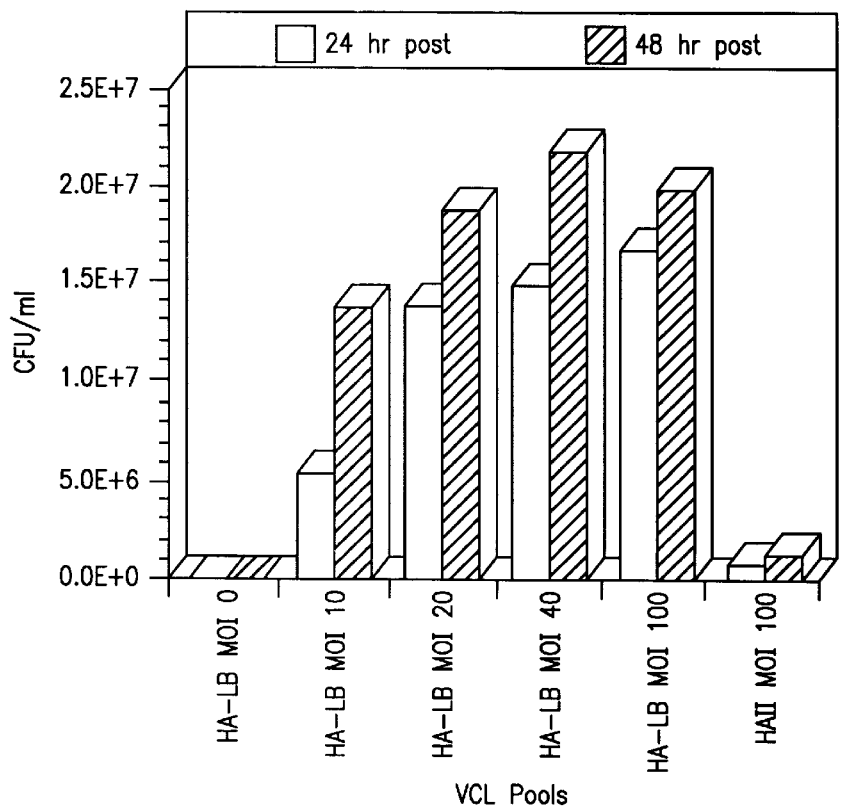
FIG. 10 is a bar graph which shows hFVIII TOE titer values for HA-LB/hFVIII VPCL pools produced at various multiplicity of transduction.

A titer analysis on supernatants from the VPCL producer pools HA-LB/hFVIII generated at mots of 10, 20, 40 and 100, was carried out as described in Example 3A-3 and 3B. VPCL pools were allowed to grow to confluency, after which they were replated at a constant cell number (0.5× $10^6$/well, 6-well plate) and again grown to confluency, fresh media added, supernatants collected and filtered (0.45 um) at multiple days post-confluency. For each supernatant, specific volumes (30, 100 and 300 ul) were used in the hFVIII TOE titer assay as described in Example 3A-3. hFVIII TOE titer results of the HA-LB/hFVIII pools derived from HA-LB PCLs seeded at $2\times10^5$ cells/well (6-well plate) and transduced for 2 consecutive days are shown in FIG. 10. FIG. 10 clearly demonstrates that increased mot for VPCL production leads to increased pool titers. In addition, the supernatants from the four HA-LB/hFVIII pools (mot 10–100) were used for a comparative titer analysis study where the hFVIII titer was determined by all three titering methods described in Example 3, namely the hFVIII TOE titer, the PCR titer and the CR titer. Titer results are shown in Table 10 and confirm that the overall titer increases with increasing mot used for pool production. The variation three titering methods is <than 4-fold with the automated PCR titer giving the and reproducible numbers.

TABLE 10 hFVIII titer analysis of HA-LB/hFVIII VPCL pools (mot 10–100) comparing three hFVIII titering methods

| HA-LB/hFVIII pools transduced with mot | TOE titer (cfu/ml) | PCR titer (cfu/ml) | PCR titer (auto.) (cfu/ml) |
|---|---|---|---|
| 10 | $4.7 \times 10^6$ | $2.2 \times 10^6$ | $8.3 \times 10^6$ |
| 20 | $1.6 \times 10^7$ | $7.2 \times 10^6$ | $2.3 \times 10^7$ |
| 40 | $3.0 \times 10^7$ | $1.2 \times 10^7$ | $3.5 \times 10^7$ |
| 100 | $4.1 \times 10^7$ | $2.3 \times 10^7$ | $5.2 \times 10^7$ |

Table 11 below describes the VPCL production process in the context of screening procedures used and numbers of hfVIII producer clones tested. Each round of a higher criterion for the titer resulting in a final number of 10 high titer shown in Table 11.

TABLE 11

Summary of screening strategy for HA-LB/hFVIII VPCL clones

|  | 1st round | 2nd round | 3rd round |
|---|---|---|---|
| Number clones screened | 384 | 80 | 25 |
| Number positive clones | 40% | 100% | 100% |
| Criterion TOE titer for expansion (cfu/ml) | $1 \times 10^7$ | $2 \times 10^7$ | $4 \times 10^7$ |

Figure 11:
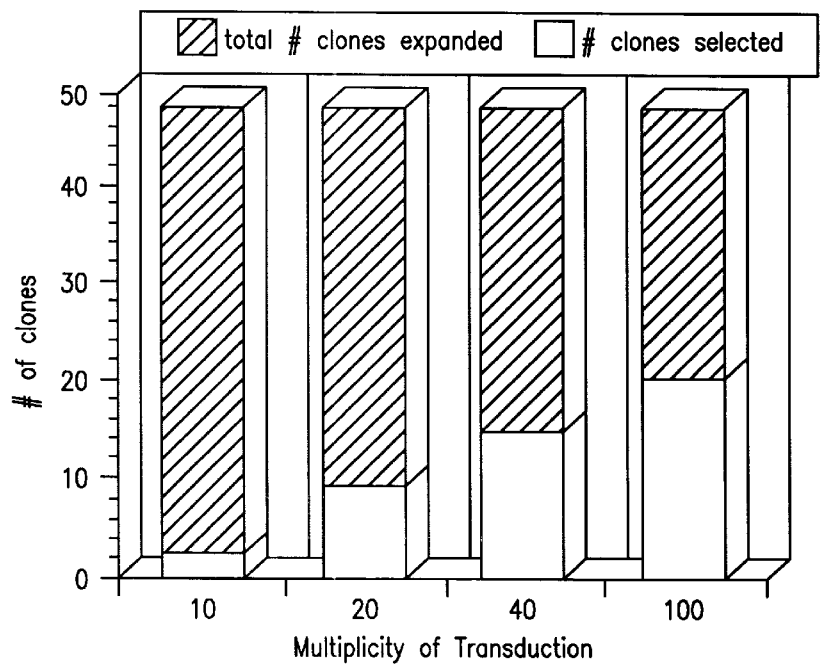
FIG. 11 is a bar graph which shows the percentage of high titer VPCL clones produced with various multiplicity of transduction.

VPCL clones were produced from all HA-LB/hFVIII pools (mot 10, 20, 40, 100) and dilution cloning carried out in 96-well plates using standard procedures. A total of 48 randomly chosen VPCL clones were expanded from each transduced pool and the number of selected clones that exceeded the final titer criterion of $4\times10^7$ cfu/ml presented in FIG. 11. FIG. 11 shows that a further benefit of the high mot approach is that a higher proportion of high titer VPCL clones was found in the higher titer pools. Therefore, dilution cloning and selecting more clones from the highest titer pool increased the overall yield of very high titer clones while minimizing the workload. The hFVIII TOE titer assay results of the final 10 high titer VPCL clones are shown in Table 12 below.

TABLE 12 hFVIII TOE titer values (3rd round of screening) of high titer
hFVIII VPCL clones derived from HA-LB transduced
with mots of 20–100

| VPCL | Clone derived from pools transduced with mot | TOE titer (cfu/ml) |
|---|---|---|
| HA-LB/hFVIII #67 | 20 | $4.2 \times 10^7$ |
| HA-LB/hFVIII #88 | 20 | $6.9 \times 10^7$ |
| HA-LB/hFVIII #87 | 20 | $8.3 \times 10^7$ |
| HA-LB/hFVIII #97 | 40 | $4.6 \times 10^7$ |
| HA-LB/hFVIII #126 | 40 | $5.8 \times 10^7$ |
| HA-LB/hFVIII #169 | 100 | $5.6 \times 10^7$ |
| HA-LB/hFVIII #152 | 100 | $6.4 \times 10^7$ |
| HA-LB/hFVIII #155 | 100 | $7.4 \times 10^7$ |
| HA-LB/hFVIII #159 | 100 | $6.7 \times 10^7$ |
| HA-LB/hFVIII #173 | 100 | $8.6 \times 10^7$ |

The potential "static" titer for top hFVIII VPCLs derived from the human PCL HA-LB with reduced RCR potential, HA-LB/hFVIII#173 is $1.0 \times 10^8$ cfu/ml.

The RCR analysis for the VPCL clones HA-LB/hFVIII#67, -87, -88, -97, -159 and -173 was carried out as described in Example 6 and all clones were found to be free of RCR.

C-3. Analysis of Set III: HA-LB/hFVIII VPCL Pools and Clones, Mot 0.1–125

This example summarizes the analysis of the hFVII VPCL pools and clones derived from transduction of the HA-LB PCL at mots of 0.1, 0.5, 5, 25 and 125. The summary describes titer and provector copy number analyses.

VPCL pools were allowed to grow to confluency, after which they were replated at a constant cell number (0.5 or $1 \times 10^6$ cells/well, 6-well plate) and again grown to confluency, fresh media added, supernatants collected and filtered (0.45 um) at multiple days post-confluency. 30, 100 and 300 ul volumes of each supernatant were used in the hFVIII TOE titer assay as described in Example 3A-3. hFVIII TOE titer results are shown in Table 13.

TABLE 13 hFVIII TOE titer results of 48 and 72 hours post-confluent
supernatant from the VPCL pools HA-LB/hFVIII mot 0.1–125

| 48 hours VPCL pools at mot 0.1–125 | hFVIII TOE titer (cfu/ml) 48 hours post-confluent | hFVIII TOE titer (cfu/ml) 72 hours post-confluent |
|---|---|---|
| HA-LB/hFVIII mot 0.1 | $2.5 \times 10^4$ | $2.7 \times 10^4$ |
| HA-LB/hFVIII mot 0.5 | $6.5 \times 10^4$ | $7.5 \times 10^4$ |
| HA-LB/hFVIII mot 5 | $6.9 \times 10^5$ | $9.1 \times 10^5$ |
| HA-LB/hFVIII mot 25 | $2.4 \times 10^6$ | $3.6 \times 10^6$ |
| HA-LB/hFVIII mot 125 | $5.9 \times 10^6$ | $5.1 \times 10^6$ |

VPCL clones were produced from all HA-LB/hFVIII pools (mot 0.5, 5 and 125) and dilution cloning carried out in 96-well plates using standard procedures. A total of 17 randomly chosen VPCL clones were expanded from the three transduced pools and the provector copy numbers determined using a Southern blot analysis as described in Example 9B-3 and the autoradiography of the Southern blot shown in FIG. 12. The HA-LB/hFVIII VPCL clones from the mot pools 0.5, 5 and 125 were also analyzed for hfVIII TOE titer. Titer results and provector copy numbers are shown in Table 14 below. This example clearly demonstrates the correlation between mot, titer and provector copy number.

TABLE 14

Summary of hFVIII TOE titer and Southern blot results on
HA-LB/VPCL clones derived from mot pools 0.5, 5 and 125.

| Clones derived from VPCL pool mot 0.5 | | | Clones derived from VPCL pool mot 5 | | | Clones derived from VPCL pool mot 125 | | |
|---|---|---|---|---|---|---|---|---|
| Clone# | Titer (cfu/ml) | provector copy# | Clone# | Titer (cfu/ml) | provector copy# | Clone# | Titer (cfu/ml) | provector copy# |
| 18 | $1.5 \times 10^6$ | 1 | 2 | $5.3 \times 10^6$ | 3–4 | 8 | $3.6 \times 10^7$ | 6–7 |
| 20 | $1.2 \times 10^6$ | 1–2 | 3 | $1.1 \times 10^6$ | n.d. | 9 | $4.1 \times 10^7$ | 7–9 |
| 26 | $6.3 \times 10^5$ | 1 | 4 | $0.7 \times 10^6$ | 2 | 13 | $3.5 \times 10^7$ | 6–9 |
| 46 | $2.4 \times 10^5$ | 1–2 | 10 | $2.7 \times 10^6$ | 1–2 | 19 | $2.5 \times 10^7$ | 7–9 |
| 49 | $5.2 \times 10^5$ | 2 | 17 | $1.6 \times 10^6$ | 3 | 22 | $2.3 \times 10^7$ | 8–9 |
| | | | | | | 23 | $2.4 \times 10^7$ | 6 |
| | | | | | | 7 | $1.4 \times 10^7$ | 6 |
| average | $8.2 \times 10^5$ | 1–2 | average | $2.3 \times 10^6$ | 2–3 | average | $2.8 \times 10^7$ | 7 |

D. Analysis of 2A-LB/IL4 Producer Pools and Clones

Figure 13:
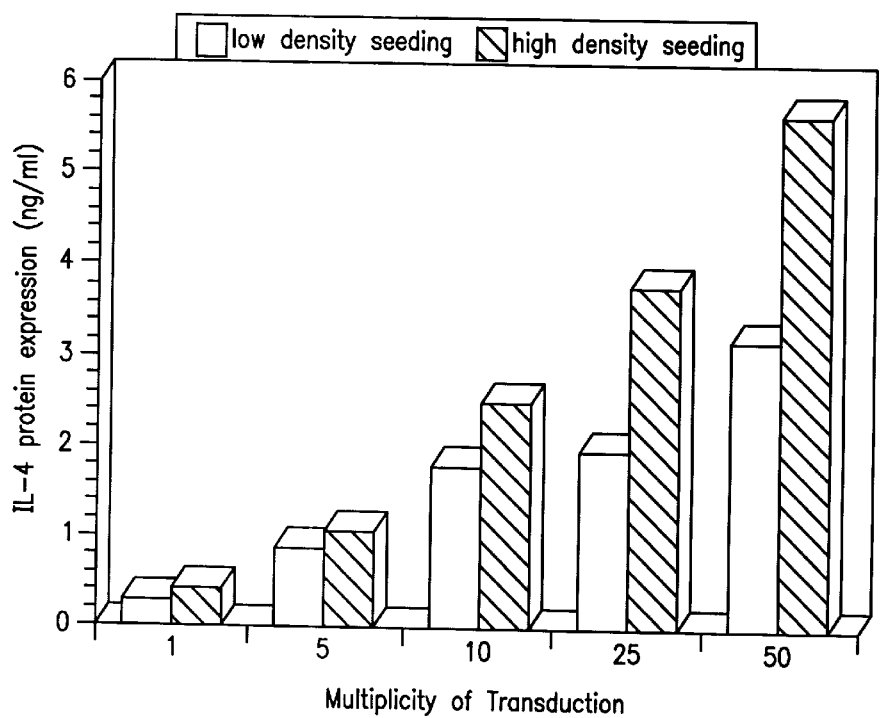
FIG. 13 is a bar graph which depicts rIL-4 TOE titers of producer pools generated with various multiplicity of transduction.

This example summarizes the titer analysis of the rIL-4 VPCL pools and clones derived from the transduction of the 2A-LB PCL with an mot of 1–50 with PCLs seeded at two densities, low (LD) and high (HD) (see Example 9D). The resulting 10 VPCL pools were grown to confluency, replated and supernatants collected at 24 and 48 hours post-confluency. 100 ul of each VPCL pool supernatant was used in the rIL-4 TOE assay (Example 3A-4) and IL-4 protein levels determined using the ELISA capture assay. Increased IL-4 expression for the different pools correlated with increased mot as shown in FIG. 13.

A total of 176 VPCL clones were produced from the most promising 2A-15 LB/rIL-4 pools (LD mot 25 pool, HD mot 10, 25 and 50 pools) using the IL-4 TOE assay, and twelve high expressing IL-4 VPCL clones selected. Ten of these 12 clones passed the screening and their PCR titers were determined as described in Example 2B and shown in Table 15.

TABLE 15

PCR titer values of selected high titer 2A-LB/rIL-4 VPCL clones

| 2A-LB/IL-4 VPCL clone# | PCR titer assay (cfu/ml) |
|---|---|
| 3 | $8.4 \times 10^6$ |
| 7 | $8.0 \times 10^6$ |
| 9 | $6.5 \times 10^6$ |
| 15 | $2.3 \times 10^6$ |
| 26 | $3.5 \times 10^6$ |
| 40 | $3.7 \times 10^6$ |
| 51 | $1.1 \times 10^7$ |
| 118 | $9.0 \times 10^6$ |
| 133 | $4.9 \times 10^7$ |
| 138 | $1.4 \times 10^6$ |

Figure 14:
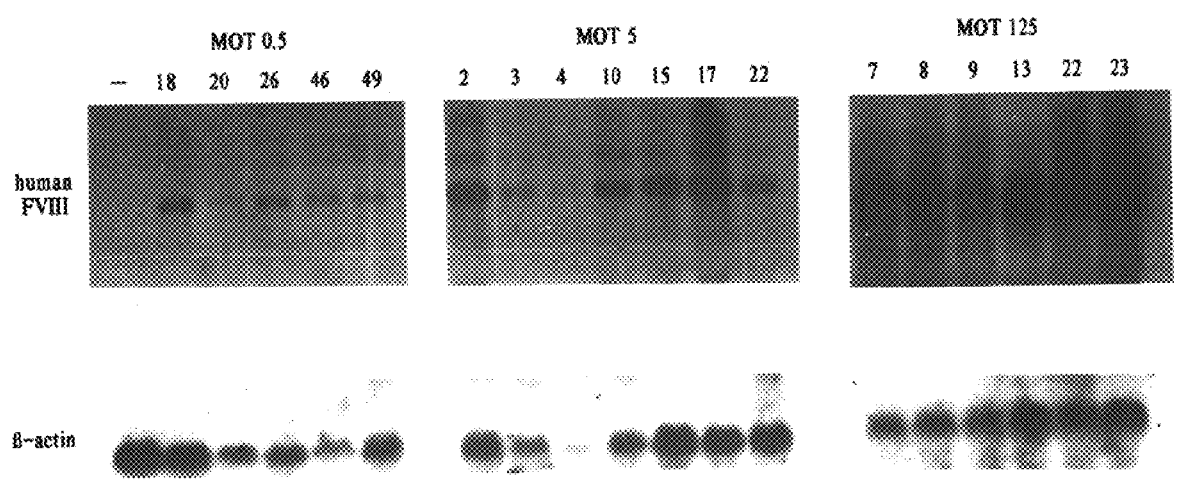
FIG. 14 is a Northern blot analysis of HA-LB hFVIII VPCL clones at several different multiplicity of transductions.

To determine whether the increased provector copy number results in increased genomic vector RNA levels, total genomic RNA was isolated from the HA-LB/VPCL lines listed in Table 14 according to standard procedures using Qiagen columns. The RNA was subjected to a Northern blot, which was probed with a hFVIII-specific probe as well as a b-actin probe for a control (FIG. 14). There is a positive correlation between provector copies/genome, vector-specific full-length RNA and titer.

E. Analysis of HA-LB/eGFP Producer Pools

This example summarizes the analysis of the eGFP VPCL pools derived from transduction of the HA-LB PCL with an mot of 9–300 (Example 8E) and results are shown in Table 16. The 6 resulting VPCL pools were seeded at equal cell densities, supernatant collected once confluent, filtered (0.45 um), HT-1080 target cells transduced and the TOE titer as well as mean fluorescence on target cells determined. Table 16 includes results from %GFP expression of the VPCL pools, TOE titer and mean fluorescence in transduced HT-1080 cells as well as %GFP expression and mean fluorescence in human PBLs transduced with supernatant from all 6 pools.

cence intensity with increasing mot which indicates that on average a higher number of pBA-9b/eGFP retroviral vectors are stably incorporated in the high mot pools when compared to the low mot pools. Furthermore, the analysis of all pool supernatants in human PBL transduction shows differences in % transduction efficiency and mean fluorescence with the highest mot pools showing the highest transduction efficiency and fluorescence in PBLs.

Briefly, human PBLs were isolated using standard procedures. Isolated PBLs were OKT-3 stimulated according to standard procedures and $0.5 \times 10^6$ PBLs resuspended in 0.5 ml of undiluted supernatant from the HA-LB/eGFP VPCL pools each. The PBLs were incubated for 2 hours at 37° C./5% CO2 in the presence of protamine sulfate at a final concentration of 5 µg/ml as an agent for increasing transduction efficiency. Then 0.5 ml medium (AIMV 7% containing 120 IU/ml of IL-2) was added and PBLs analyzed 72 hours post-transduction. Transduction of PBLs with 1:4 diluted supernatant was carried out accordingly.

Example 10

Generation of High Titer Vector Material Over Several Days Under Scale-Up Conditions The highest titer HAII/hFVIII and HA-LB/hFVIII derived VPCL clones generated using the high mot transduction and clone selection protocol, were compared to the DA-derived hFVIII producer DA/B-del-1 (described in WO 98/00541) regarding titer output over time under scale-up conditions.

Large scale retroviral vector production utilized a static culture expansion train. Initially 225 cm² tissue culture flasks were inoculated and the cells cultured using DMEM media formulated with 10% γ-irradiated defined fetal bovine serum for 3–4 days until just subconfluent, and then progressively passaged while increasing the surface area to 4×10-layer cell factories (Nalge Nunc International, IL) prior to bioreactor inoculation. Large scale production utilized the CellCube™ (Coming Costar Inc., MA) perfusion

TABLE 16

Summary of HA-LB/eGFP producer pool analysis

| VPCL pool transduced with mot 9-300 | % eGFP expression in pools | Mean fluorescence in pools | Titer in HT-1080 (cfu/ml) | % eGFP expressing PBLs (undil./1:4 dil.) | Mean fluorescence in transduced PBLs (undil./1:4 dil.) |
|---|---|---|---|---|---|
| HA-LB/eGFP mot 300 | 96 | 5002 | $1.2 \times 10^7$ | 3.8/8.0 | 701/782 |
| HA-LB/eGFP mot 150 | 96 | 4924 | $1.0 \times 10^7$ | –/– | –/– |
| HA-LB/eGFP mot 75 | 94 | 2195 | $1.1 \times 10^7$ | 2.7/4.2 | 765/739 |
| HA-LB/eGFP mot 37.5 | 93 | 3649 | $1.2 \times 10^7$ | 1.8/5.1 | 449/662 |
| HA-LB/eGFP mot 19 | 92 | 3203 | $1.3 \times 10^7$ | 2.2/3.5 | 555/635 |
| HA-LB/eGFP mot 9 | 92 | 2529 | $1.3 \times 10^7$ | –/– | –/– |

Figure 15:
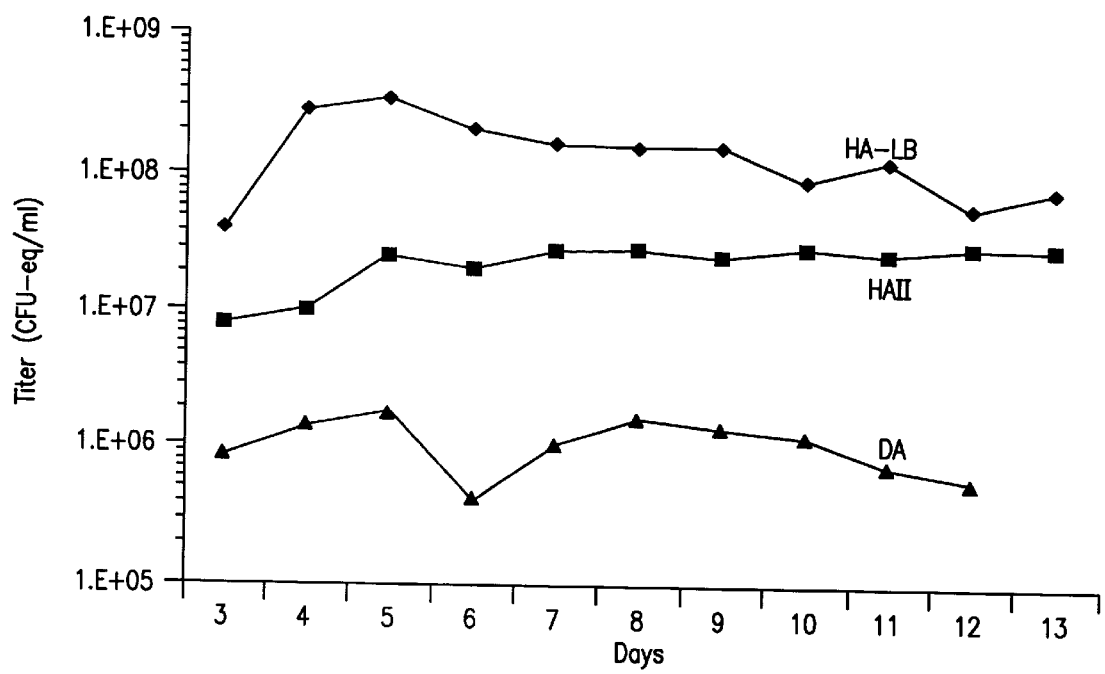
FIG. 15 is a graph which shows the titer of various clones over a period 12 to 13 days.

The range of mots chosen does not indicate an increase of titer in HT-1080 target cells between an mot ranging from 9 to 300. All VPCL pools are ≧92% eGFP positive and all pools have a titer of $1 \times 10^7$ cfu/ml which is extremely high, indicating that most likely pool titers at an mot <9 will be lower than $1 \times 10^7$ cfu/ml. However, the analysis of all VPCL producer pools show the trend of increasing mean fluoresfed cell culture system. Production media was a custom DMEM (Hyclone, UT) formulated with 10% γ-irradiated FBS (Hyclone, UT). Perfusion was controlled based on glucose consumption and up to a maximum media exchange of 8 system volumes per day. Production volume ranged from 200 to 400 liters over a period of up to 13 days. Over 13 days in culture, the new high titer producer clones consistently generate 1–2 magnitudes higher titer compared to the DA/B-del-1 line. Results are shown in FIG. 15.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated retroviral vector particle producing cell, wherein said cell (a) has greater than 5 stably integrated copies of a retroviral vector construct; (b) produces greater than 10 infectious recombinant retroviral vector particles per cell per day; (c) produces replication incompetent retroviral vector particles, wherein said cell stably produces infectious recombinant retroviral vector particles over at least 50 cell doublings.

2. The isolated retroviral vector particle producing cell according to claim 1 wherein said cell has greater than 8 stably integrated copies of a retroviral vector construct.

3. The isolated retroviral vector particle producing cell according to claim 1 wherein said cell produces greater than 20 infectious recombinant retroviral vector particles per cell per day.

4. The isolated retroviral vector particle producing cell according to claim 1 wherein said cell has a stably integrated gag/pol expression cassette.

5. The isolated retroviral vector particle producing cell according to claim 1 wherein said cell has a stably integrated gag expression cassette and a stably integrated pot expression cassette.

6. The isolated retroviral vector particle producing cell according to claim 1 wherein said cell has a stably integrated env expression cassette.

7. The isolated retroviral vector particle producing cell according to claim 6 wherein said env expression cassette is a VSV-G expression cassette.

8. A method for producing high titer recombinant retroviral vector particle producing cells, comprising transducing greater than 20 recombinant retroviral vector particles per cell into a population of packaging cells, wherein said cells stably produce infectious recombinant retroviral vector particles over at least 50 cell doublings.

9. A method for producing recombinant retroviral vector particle producing cells, comprising transfecting recombinant retroviral vector constructs into a population of packaging cells, wherein at least 5 retroviral vector constructs per cell are stably integrated into said cells, wherein said cells stably produce infectious recombinant retroviral vector particles over at least 50 cell doublings.

10. The method according to claim 8 or 9 wherein said packaging cell has a stably integrated gag/pol expression cassette.

11. The method according to claim 10 wherein said gag/pol expression cassette does not have envelope coding sequences.

12. The method according to claim 9 wherein said env expression cassette does not have sequence which overlaps with the retroviral vector construct.

13. The method according to claim 8 or 9 wherein said packaging cell has a stably integrated gag expression cassette and a stably integrated pol expression cassette.

14. A method for producing recombinant retroviral vector particle producing cells, comprising:
    (a) generating VSV-G pseudotyped retroviral vector particles;
    (b) concentrating said particles;
    (c) introducing said vector particles into a packaging cell line, such that recombinant retroviral vector particle producing cells are produced; wherein said cells stably produce infectious recombinant retroviral vector particles over at least 50 cell doublings.

15. The method according to claim 14 wherein greater than 5 stably integrated copies of a retroviral vector construct are produced in said retroviral vector particle producing cell.

* * * * *